US012723125B2

(12) United States Patent
Pramanik et al.

(10) Patent No.: US 12,723,125 B2
(45) Date of Patent: Sep. 1, 2026

(54) ENVIRONMENTALLY BIODEGRADABLE COMPOSITIONS COMPRISING AN AMINO ACID ADDUCT, CONTROLLED RELEASE PARTICLES AND COMPOSITIONS COMPRISING SAME, AND METHODS OF MAKING SAME

(71) Applicant: TRUCAPSOL LLC, Bethlehem, PA (US)

(72) Inventors: Monoj Pramanik, Allentown, PA (US); Jiten Dihora, Center Valley, PA (US)

(73) Assignee: TRUCAPSOL LLC, Bethlehem, PA (US)

( * ) Notice: Subject to any disclaimer, the term of this patent is extended or adjusted under 35 U.S.C. 154(b) by 331 days.

(21) Appl. No.: 18/643,585

(22) Filed: Apr. 23, 2024

(65) Prior Publication Data

US 2025/0326882 A1 Oct. 23, 2025

(51) Int. Cl.

| | |
|---|---|
| ***C08G 18/28*** | (2006.01) |
| ***A61K 8/11*** | (2006.01) |
| ***A61K 9/00*** | (2006.01) |
| ***C08G 77/04*** | (2006.01) |
| ***C08L 5/08*** | (2006.01) |

(52) U.S. Cl.

CPC .............. *C08G 18/287* (2013.01); *A61K 8/11* (2013.01); *A61K 9/0004* (2013.01); *C08G 77/04* (2013.01); *C08L 5/08* (2013.01)

(58) Field of Classification Search

None

See application file for complete search history.

(56) References Cited

U.S. PATENT DOCUMENTS

| | | | |
|---|---|---|---|
| 3,870,542 | A | 3/1975 | Ida et al. |
| 3,932,359 | A | 1/1976 | Fujimoto et al. |
| 4,626,471 | A | 12/1986 | Chao |
| 4,686,242 | A | 8/1987 | Turner et al. |
| 4,835,224 | A | 5/1989 | Ruckes et al. |
| 5,126,151 | A | 6/1992 | Bodor et al. |
| 5,574,179 | A | 11/1996 | Wahl et al. |
| 6,248,909 | B1 | 6/2001 | Akimoto et al. |
| 6,544,926 | B1 | 4/2003 | Bodmer et al. |
| 7,122,503 | B2 | 10/2006 | Seehafer et al. |
| 8,071,214 | B2 | 12/2011 | Schwantes |
| 8,357,651 | B2 | 1/2013 | Quellet et al. |
| 9,359,464 | B2 | 6/2016 | Berthier et al. |
| 9,937,477 | B2 | 4/2018 | Zhang et al. |
| 9,944,886 | B2 | 4/2018 | Hitchcock et al. |
| 9,993,401 | B2 | 6/2018 | Barnett et al. |
| 10,188,593 | B2 | 1/2019 | Dihora et al. |
| 11,007,501 | B2 | 5/2021 | Bachawala |
| 11,034,920 | B2 | 6/2021 | Struillou et al. |
| 11,179,302 | B2 | 11/2021 | Dardelle |
| 11,344,502 | B1 | 5/2022 | Dihora et al. |
| 11,465,117 | B2 | 10/2022 | Bachawala et al. |
| 11,484,857 | B2 | 11/2022 | Bachawala et al. |
| 11,542,392 | B1 | 1/2023 | Multari |
| 11,547,978 | B2 | 1/2023 | Bachawala et al. |
| 11,571,674 | B1 | 2/2023 | Dihora et al. |
| 11,794,161 | B1 | 10/2023 | Dihora et al. |
| 11,878,280 | B2 | 1/2024 | Khanal et al. |
| 11,904,288 | B1 | 2/2024 | Dihora et al. |
| 11,969,491 | B1 | 4/2024 | Dihora et al. |
| 12,187,829 | B2 | 1/2025 | Dihora et al. |
| 12,302,933 | B2 | 5/2025 | Dihora |
| 2008/0167188 | A1 | 7/2008 | Fischer et al. |
| 2011/0268778 | A1 | 11/2011 | Dihora et al. |
| 2012/0148644 | A1 | 6/2012 | Popplewell et al. |
| 2012/0157620 | A1 | 6/2012 | Nagy et al. |
| 2013/0089590 | A1 | 4/2013 | Hotz et al. |
| 2015/0252312 | A1 | 9/2015 | De Villeneuve et al. |
| 2018/0015009 | A1 | 1/2018 | Soubiran et al. |
| 2021/0237020 | A1* | 8/2021 | Bachawala ............. A23L 27/72 |
| 2021/0261885 | A1 | 8/2021 | Tibbs et al. |

(Continued)

FOREIGN PATENT DOCUMENTS

| | | | |
|---|---|---|---|
| EP | 4265326 | A2 | 10/2023 |
| GB | 1502440 | A | 3/1978 |

(Continued)

OTHER PUBLICATIONS

English Abstract for WO 2020195132 A1 (2020).

(Continued)

*Primary Examiner* — Susan T Tran

*Assistant Examiner* — William Craigo

(74) *Attorney, Agent, or Firm* — Caesar Rivise, PC

(57) ABSTRACT

Disclosed is a controlled release particle including a core including at least one hydrophobic active ingredient, optionally a sugar alcohol, and optionally a plasticizer; and a shell including a reaction product of (a) at least one isocyanate resin and at least one epoxy resin with (b) at least one treated protein isolate, at least one mono epoxy alkoxy silane, at least one hydrolyzed organofunctional silane, at least one gelatinized polysaccharide, at least one amino polysaccharide and at least one adduct. The at least one adduct is at least one amine-acid functional urea linked amino acid isocyanate adduct and/or at least one amine-hydroxy-acid functional amino acid epoxide adduct. Further disclosed are a controlled release composition including a plurality of the particles, and a method of making the controlled release particle.

18 Claims, 2 Drawing Sheets

(56) References Cited

U.S. PATENT DOCUMENTS

| | | | | |
|---|---|---|---|---|
| 2022/0133603 | A1* | 5/2022 | Bachawala | B01J 13/16 424/401 |
| 2022/0177815 | A1 | 6/2022 | Popplewell et al. | |
| 2022/0194803 | A1 | 6/2022 | Inokuchi | |

FOREIGN PATENT DOCUMENTS

| | | | |
|---|---|---|---|
| WO | 2006024411 | A2 | 3/2006 |
| WO | 2008118133 | A1 | 10/2008 |
| WO | 2011041395 | A1 | 4/2011 |
| WO | 2015091877 | A1 | 6/2015 |
| WO | 2020195132 | A1 | 10/2020 |

OTHER PUBLICATIONS

ECHA Microplastic Biodegradability Requirements (2019).
Gasparini et al., "Quantification of Residual Perfume by Py-GC-MS in Fragrance Encapsulate Polymeric Materials Intended for Biodegradation Tests," Molecules, vol. 25, 2020, 718.
OECD (1992) Test No. 301, Ready Biodegradability, OECD Guidelines for the Testing of Chemicals, Section 3. https://doi.org/10.1787/9789264070349-en.

* cited by examiner

ENVIRONMENTALLY BIODEGRADABLE COMPOSITIONS COMPRISING AN AMINO ACID ADDUCT, CONTROLLED RELEASE PARTICLES AND COMPOSITIONS COMPRISING SAME, AND METHODS OF MAKING SAME

BACKGROUND OF THE INVENTION

1. Field of Invention

This invention relates to controlled release capsule compositions, encapsulation compositions and methods for making and using them.

2. Description of Related Art

There are many microencapsulated delivery systems disclosed in the art to control the release of the encapsulated active, or provide release when a specific trigger is applied. Such systems have previously suffered from a number of drawbacks.

Controlled release microcapsules that provide release of active upon application of shear or friction generally suffer from several drawbacks: (1) such microcapsules are made of highly crosslinked membranes and membrane materials that cannot be broken down by microbes found in the environment, (2) despite such highly crosslinked membranes, the materials of construction of the membrane impart high permeabilities when incorporated into products that contain high levels of surfactant, solvents, and/or water, which results in the premature benefit agent release, (3) they can only effectively encapsulate a limited breadth of benefit agents, (4) they either are so stable that they do not release the benefit agent in use or have insufficient mechanical stability to withstand the processes required to incorporate them in and/or make a consumer product, (5) they do not adequately deposit on the surface that is being treated with consumer product that contains microcapsules, (6) the dry powder form of such controlled release microcapsules do not redisperse well when formulated into aqueous formulations, and/or (7) they do not comprise membrane materials that have a favorable environmental degradability profile.

In general, conventional microcapsules have a structure of an encapsulated active composition enclosed in a polymeric shell. The microcapsules have a polymeric shell which is generally obtained by any one of: (a) condensation reactions, (b) free radical polymerization reactions, (c) interfacial polymerization reactions, or (d) coacervation of preformed polymers followed by crosslinking of the thereby obtained coacervates by using a crosslinker.

There is a challenge in designing a polymeric shell membrane that minimizes the diffusion of the encapsulated active into the surrounding formulation, and yet is environmentally biodegradable. Environmentally biodegradable polymers generally swell in water, or are soluble in water. In contrast, microcapsule membranes generally need to resist swelling or dissolution in aqueous cleaning product formulation. A high degree of crosslinking within the membrane can reduce swelling and solubility; however, such highly crosslinked membranes are difficult for environmentally available microbes to digest and breakdown.

There are four main types of core/shell microcapsules commercialized in industry: aminoplast made via condensation, polyurea made via interfacial polymerization, polyacrylate made via free radical polymerization, and complex coacervate capsules made via hardening a coacervate of gelatin and gum Arabic.

Aminoplast capsules comprise a core of hydrophobic active material surrounded by a polyurea shell. The shell is the result of a condensation reaction of methylolated urea or methylolated melamine catalyzed by acidic conditions. U.S. Pat. No. 8,357,651B2, U.S. Pat. No. 7,122,503B2, GB1502440A and U.S. Pat. No. 9,359,464B2 provide detailed information on the preparation of such capsules.

Polyurea capsules made via interfacial polymerization of isocyanates and amines are disclosed in WO2020195132A1. The application discloses polyisocyanates dissolved in an oil phase, and the amines dissolved in the water phase. These two materials come together at the oil/water interface to produce a polyurea reaction product. The capsules have porous shells that cause premature leakage of the encapsulated active, and such polyurea membranes have less than 30% environmental biodegradability (OECD 301D, 60 days). US20130089590A1 and US20120148644A1 also provide details on the preparation of polyurea capsules via the use of isocyanates.

Polyacrylate capsules made via free radical polymerization are disclosed in U.S. Pat. No. 9,937,477B2. The patent discloses core/shell microcapsules that are manufactured using free radical polymerization of acrylates. Such microcapsules require multi-step reactions that require heating the capsules to 95° C. for up to 6 hours. It is well known that such highly crosslinked polyacrylate shells have poor environmental biodegradability. U.S. Pat. No. 8,071,214B2 (Encapsys) also provides details on preparation of acrylate capsules via free radical polymerization.

Complex coacervate capsules are disclosed in U.S. Pat. No. 6,544,926B1 (Encapsys).

Often, it is desired to transform the aqueous suspension of microcapsules into a dry powder for several reasons. First, transportation costs are reduced as a result of shipping less water. Second, lower energy use during transport reduces the carbon footprint. Third, an aqueous slurry requires the use of preservatives to minimize microbial activity. Fourth, an aqueous slurry requires suspension agents to maintain phase stability of the microcapsules. Fifth, the shelf life of dry powders is much longer than that of a liquid suspension of capsules. Transforming a slurry of such capsules disclosed in the art into a dry powder is challenging. Spray drying the suspension of capsules to remove water results in fracture of microcapsules due to particle-particle collisions during the drying process. U.S. Pat. No. 11/034,920B2 discloses the use of maltodextrin and modified starch as carriers to facilitate the drying of aminoplast capsules. Large volumes of water are necessary to redisperse the spray dried capsules due to the nature of the modified starch. It would be difficult to disperse these capsules in liquid fabric softener or liquid detergent formulations without forming aggregates. Such aggregates physically separate from the liquid formulation. Such aggregates, if not properly broken down during the laundering process, appear as residue on fabrics. Moreover, aminoplast capsules are not environmentally biodegradable. Aminoplast capsules also have high leakage (greater than 20%) of the encapsulated oil when formulated in laundry formulations.

While others have attempted to improve the barrier properties of microcapsules, there remains significant shortcomings and limitations in the art. For example, U.S. Pat. No. 9,944,886B2 (Hitchcock) describes metal coated microcapsules with improved barrier properties. The Hitchcock metal coating is developed after the formation of the microcapsule membrane, via the use of a sterically stabilized nanosuspension of metal particle. Such metal coated microcapsules could improve barrier properties; however, it is difficult to imagine how the encapsulated active would be released, since a metal coating would be difficult to fracture. Furthermore, the processing steps involved to achieve the metal coating are laborious and expensive. Moreover, such metal coating could render the microcapsules non-environmentally biodegradable.

Conventional controlled release particles that comprise a core and a shell have several limitations. First, such capsules prematurely release the active material when suspended in a finished product formulations, such as cleaning product formulations. Second, such capsules have poor environmental biodegradability due to the nature of materials used and the degree of crosslinking that is achieved in order to reduce the diffusion of the active. Third, it is difficult to control the release profile of the encapsulated active. Fourth, poor adhesion of particles to the substrate results in significant loss of the particles, especially when formulations containing such particles are used in rinse-off applications. Examples of such applications include laundering fabrics, shampooing hair, conditioning hair, cleansing the skin, showering, and the like. In such applications, a composition comprising microcapsules is applied to a substrate to initiate cleaning, and subsequently the composition is removed by using water. Fifth, dry powder form of these microcapsules is difficult to redisperse into liquid formulations.

Accordingly, it is desired to provide microcapsules and a method of using them to remove soil and dirt from a substrate, while retaining the microcapsules containing active materials on the substrate through the rinsing process.

It is further desired to provide a means to manipulate the release profile of the encapsulated active.

It is further desired to provide microcapsules whose membranes have an environmental biodegradability greater than 50%, achievable with very minor changes in existing commercial scale processes to make such microcapsules.

Hence, it is desired to provide low permeability microcapsules that can retain the encapsulated active in concentrated surfactant containing solutions, or under highly dilute aqueous conditions. It is further desired to improve the adhesion of microcapsules onto the desired substrate during rinse-off applications. It further is desired to release the encapsulated active in larger quantities, and over a longer duration of time. It is further desired to have capsules that have a favorable environmental biodegradability profile as defined by OECD 301D method (OECD 1992, Test No. 301 Ready Biodegradability, OECD Guidelines for the Testing of Chemicals, Section 3, OECD Publishing, Paris, https://doi.org/10.1787/9789264070349-en).

All references cited herein are incorporated herein by reference in their entireties. The citation of any reference is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

BRIEF SUMMARY OF THE INVENTION

Accordingly, a first aspect of the invention is a controlled release particle comprising:

- a core that comprises at least one hydrophobic active ingredient, optionally a sugar alcohol, and optionally a plasticizer; and
- a shell that comprises a reaction product of (a) at least one isocyanate resin and at least one epoxy resin with (b) at least one treated protein isolate, at least one mono epoxy alkoxy silane, at least one hydrolyzed organofunctional silane, at least one gelatinized polysaccharide, at least one amino polysaccharide and at least one adduct, wherein the at least one adduct is at least one of:
- (i) at least one amine-acid functional urea linked amino acid isocyanate (AAI) adduct having a structure represented by Formula I:

Formula I

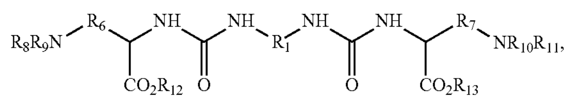

and salts thereof, and

- (ii) at least one amine-hydroxy-acid functional amino acid epoxide (AAE) adduct having a structure represented by Formula II:

Formula II

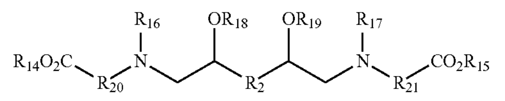

and salts thereof, where

- $R_1$ is a moiety of a monomer or a prepolymer comprising two —NCO functional groups wherein the NCO functional groups have reacted to form urea linkages;
- $R_2$ is a moiety of a monomer or a prepolymer comprising two glycidyl ether epoxide functional groups wherein the epoxide groups have reacted to form amino alcohol groups;
- $R_6$, $R_7$, $R_{20}$ and $R_{21}$ are each independently $(CH_2)_n$, wherein n is 1-6;
- $R_8$, $R_9$, $R_{10}$ and $R_{11}$ are each independently hydrogen or $CH_2X$;
- $R_{12}$ and $R_{13}$ are each independently hydrogen, an alkali metal cation, or X;
- $R_{14}$ and $R_{15}$ are each independently hydrogen, an alkali metal cation, or X;
- $R_{16}$ and $R_{17}$ are each independently hydrogen or X;
- $R_{18}$ and $R_{19}$ are each independently hydrogen, $SiO_3$ or X; and
- each occurrence of X is independently selected from the group consisting of hydrogen and a substituent.

In certain embodiments, the controlled release particle has a biodegradability greater than 60% measured according to OECD 301D.

In certain embodiments, the controlled release particle comprises the at least one AAI adduct, wherein: $R_6$ and $R_7$ are each $(CH_2)_4$; $R_8$, $R_9$, $R_{10}$ and $R_{11}$ are each hydrogen; and $R_{12}$ and $R_{13}$ are each independently hydrogen or an alkali metal cation.

In certain embodiments, the controlled release particle comprises the at least one AAE adduct, wherein: $R_{14}$ and $R_{15}$ are each independently hydrogen or an alkali metal cation; $R_{16}$ and $R_{17}$ are each hydrogen; $R_{18}$ and $R_{19}$ are each independently hydrogen or $SiO_3$; and $R_{20}$ and $R_{21}$ are each $(CH_2)_2$.

In certain embodiments, the shell comprises a polymer comprising more than one of the at least one AAI adduct or more than one of the at least one AAE adduct.

In certain embodiments, the shell comprises a copolymer comprising at least one of the AAI adduct and at least one of the AAE adduct.

In certain embodiments, the core comprises the sugar alcohol, which is an alcohol of a monosaccharide, disaccharide, trisaccharide, tetra-saccharide or penta-saccharide.

In certain embodiments, the core comprises the plasticizer, which is a member selected from the group consisting of methyl esters of rosin, polyazelate esters, di-fatty acid esters, citrate esters, polyadipate esters and polyester resins consisting of inner and intra-esters of polyhydroxy carboxylic acids.

In certain embodiments, the hydrophobic active ingredient is a member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

In certain embodiments, the at least one treated protein isolate is a member selected from the group consisting of proteinogenic L-amino acids, animal protein, plant protein, animal protein hydrolysate, plant protein hydrolysate, animal protein produced by physicochemical or fermentative or enzymatic treatment, and plant protein produced by physicochemical or fermentative or enzymatic treatment.

In certain embodiments, the at least one mono epoxy alkoxy silane is a member selected from the group consisting of alkoxylated silane, trialkoxy silanes, functionalized trialkoxysilanes, tetraalkoxylated silanes, 1,2-bis(triethoxysilyl)ethane and glycidoxyalkyltrialkoxy.

In certain embodiments, the at least one hydrolyzed organofunctional silane is a member selected from the group consisting of hydrolyzed alkoxylated silanes, hydrolyzed trialkoxy silanes, hydrolyzed tetraalkoxylated silanes, and hydrolyzed glycidyl ether silanes.

In certain embodiments, the at least one gelatinized polysaccharide is a member selected from the group consisting of tapioca, potato, corn, rice, wheat, carboxy modified polysaccharide, waxy maize starch, pre-gelatinized starch, pregelatinized polysaccharide, pre-gelatinized waxy maize starch, octenyl succinic anhydride modified starch, anionically modified starch and cationically modified starch.

In certain embodiments, the at least one amino polysaccharide is a member selected from the group consisting of amino polysaccharide (chitosan), chitosan oligosaccharide and carboxymethyl chitosan.

In certain embodiments, the controlled release particle has a diameter of 1-150 μm.

A second aspect of the invention is a controlled release composition comprising more than one said controlled release particle of the invention, wherein the controlled release composition is a consumer product selected from the group consisting of a powdered food product, a fluid food product, a powdered nutritional supplement, a fluid nutritional supplement, a fluid fabric enhancer, a solid fabric enhancer, a fluid shampoo, a solid shampoo, a hair conditioner, a body wash, a solid antiperspirant, a fluid antiperspirant, a solid deodorant, a fluid deodorant, a fluid detergent, a solid detergent, a fluid hard surface cleaner, a solid hard surface cleaner, a fluid fabric refresher spray, a diaper, an air freshening product, a nutraceutical supplement, a controlled release fertilizer, a controlled release insecticide, a controlled release dye and a unit dose detergent further comprising a detergent and a water soluble outer film.

A third aspect of the invention is a method of making the controlled release particle of the invention, said method comprising the steps of: (a) preparing a core material phase by mixing at least one hydrophobic active material with at least one isocyanate resin or prepolymer, at least one epoxy resin or prepolymer, a glycidyloxy alkyl trialkoxy silane, a sugar alcohol and a polymeric plasticizer to make a solution or suspension; (b) preparing a homogeneous aqueous solution or aqueous dispersion of at least one emulsifier or surfactant and treated protein isolate solution or dispersion; (c) adding the core material phase into the homogeneous aqueous solution or aqueous dispersion to prepare an oil-in-water emulsion at 20-35° C.; (d) adjusting a pH and heating the oil-in-water emulsion at 35-40° C. to form a preformed capsule slurry via interfacial polymerization; (e) adding an aqueous solution of at least one of the at least one AAI adduct, and the at least one AAE adduct into the preformed capsule slurry to form an emulsion; (f) heating the emulsion to a temperature from 40-60° C. for further polymerization onto a preformed capsule membrane; (g) adding tetrahydroxy orthosiloxane or orthosilicic acid to the preformed capsule membrane for further crosslinking or polymerization to provide a capsule; (h) adding a fine powder of amino polysaccharide to form a coacervate on a surface of the capsule; (i) adding an aqueous dispersion of treated or gelatinized polysaccharide to the capsule to provide a capsule slurry; (j) optionally, adding preservative into the capsule slurry; and (k) spray drying the capsule slurry to obtain dry powder.

In certain embodiments of the method, the at least one emulsifier is a member selected from the group consisting of natural gum, polyvinyl pyrrolidone, copolymer of polyvinyl pyrrolidone with vinyl acetate, vinyl alcohol, vinyl imidazole, polyglycerol oleate, polyvinyl alcohol, ethoxylate nonylphenol, secondary alcohol ethoxylate, water soluble protein, modified polysaccharide, Pickering emulsion stabilizer and chitosan.

BRIEF DESCRIPTION OF THE DRAWINGS

The invention will be described in conjunction with the following drawings, wherein.

DETAILED DESCRIPTION OF PREFERRED EMBODIMENTS OF THE INVENTION

Glossary

Figure 1:
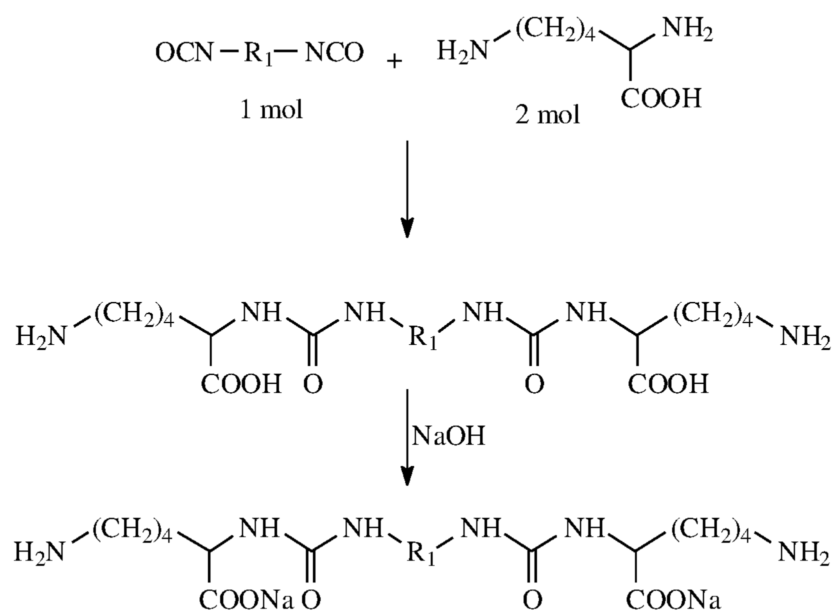
FIG. 1 is a non-limiting example of a synthetic scheme for the preparation of an embodiment of an amino acid isocyanate adduct in accordance with the first aspect of the invention.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from the group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, unless otherwise noted, the terms "capsule", "microcapsule" and "particle" are synonyms, which refer to containers for selectively retaining an active ingredient.

As used herein, unless otherwise noted, the terms "shell," "membrane" and "wall" are synonyms, which refer to barriers at least partially surrounding the core of the particles of the invention.

As used herein, microcapsules "formed under acidic conditions" means that part of the process of forming the microcapsule involves a step where the pH of the suspension in which the microcapsules form is adjusted into the acidic region (less than 7).

As used herein, microcapsules "formed under basic conditions" means that part of the process of forming the microcapsule involves a step where the pH of the suspension in which the microcapsules form is adjusted into the alkaline region (greater than 7).

As used herein, "an unreacted amount" refers to the amount of a reactant not used up in one or more reaction. "An unreacted amount" can be zero to any amount depending on the amount of reactants added.

As used herein, unless otherwise noted, "alkyl" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups, the alkyl groups may be the same or different.

The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like.

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

As used herein "cleaning and/or treatment compositions" means products comprising fluid laundry detergents, fabric enhancers, laundry and/or rinse additives, fluid dishwashing detergents, fluid hard surface cleaning and/or treatment compositions, fluid toilet bowl cleaners that may or may not be contained in a unit dose delivery product all for consumer, agricultural, industrial or institutional use.

The term "absorbent article" is used herein in a very broad sense including any article able to receive and/or absorb and/or contain and/or retain fluids and/or exudates, especially bodily fluids/bodily exudates. Exemplary absorbent articles in the context of the present invention are disposable absorbent articles.

The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical disposable absorbent articles according to the present invention are diapers, surgical and wound dressings, breast and perspiration pads, incontinence pads and pants, bed pads as well as absorbent articles for feminine hygiene like sanitary napkins, panty liners, tampons, interlabial devices or the like. Absorbent articles suitable for use in the present invention include any type of structures, from a single absorbent layer to more complex multi-layer structures. Certain absorbent articles include a fluid pervious topsheet, a backsheet, which may be fluid impervious and/or may be water vapor and/or gas pervious, and an absorbent element comprised there between, often also referred to as "absorbent core" or simply "core".

The term "Sanitary tissue product" or "tissue product" as used herein means a wiping implement for post-urinary and/or post-bowel movement cleaning (toilet tissue products), for otorhinolaryngological discharges (facial tissue products) and/or multi-functional absorbent and cleaning uses (absorbent towels such as paper towel products and/or wipe products). The sanitary tissue products of the present invention may comprise one or more fibrous structures and/or finished fibrous structures, traditionally, but not necessarily, comprising cellulose fibers.

The term "tissue-towel paper product" refers to products comprising paper tissue or paper towel technology in general, including, but not limited to, conventional felt-pressed or conventional wet-pressed tissue paper, pattern densified tissue paper, starch substrates, and high bulk, uncompacted tissue paper. Non-limiting examples of tissue-towel paper products include towels, facial tissue, bath tissue, table napkins, and the like.

"Personal care composition" refers to compositions intended for topical application to skin or hair and can be, for example, in the form of a liquid, semi-liquid cream, lotion, gel, or solid. Examples of personal care compositions can include, but are not limited to, bar soaps, shampoos, conditioning shampoos, body washes, moisturizing body washes, shower gels, skin cleansers, cleansing milks, in-shower body moisturizers, pet shampoos, shaving preparations, etc.

"Bar soap" refers to compositions intended for topical application to a surface such as skin or hair to remove, for example, dirt, oil, and the like. The bar soaps can be rinse-off formulations, in which the product is applied topically to the skin or hair and then subsequently rinsed within minutes from the skin or hair with water. The product could also be wiped off using a substrate. Bar soaps can be in the form of a solid (e.g., non-flowing) bar soap intended for topical application to skin. The bar soap can also be in the form of a soft solid which is compliant to the body. The bar soap additionally can be wrapped in a substrate which remains on the bar during use.

"Rinse-off" means the intended product usage includes application to skin and/or hair followed by rinsing and/or wiping the product from the skin and/or hair within a few seconds to minutes of the application step.

"Ambient" refers to surrounding conditions at about one atmosphere of pressure, 50% relative humidity and about 25° C.

"Anhydrous" refers to compositions and/or components which are substantially free of added or free water.

"Antiperspirant composition" refers to antiperspirant compositions, deodorant compositions, and the like. For example, antiperspirant creams, gels, soft solid sticks, body sprays, and aerosols.

"Soft solid" refers to a composition with a static yield stress of about 200 Pa to about 1,300 Pa. The term "solid" includes granular, powder, bar and tablet product forms.

The term "fluid" includes liquid, gel, paste and gas product forms.

The term "dry matter in the controlled release particle" refers to the mass of all ingredients in the controlled release particle after subtracting water.

The term "situs" includes paper products, fabrics, garments, hard surfaces, hair and skin.

The term "substantially free of" refers to 2% or less of a stated ingredient. "Free of" refers to no detectable amount of the stated ingredient or thing.

As used herein, the terms "a" and "an" mean "at least one".

As used herein, the terms "include", "includes" and "including" are meant to be non-limiting.

Unless otherwise noted, in discussing the commercial applications below, all component or composition levels are in reference to the active portion of that component or composition, and are exclusive of impurities, for example, residual solvents or byproducts, which may be present in commercially available sources of such components or compositions.

Similarly, all percentages and ratios are calculated by weight unless otherwise indicated and are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Advantages of the Invention

Advantages of the invention include but are not limited to one or more of the following benefits provided by preferred embodiments of the invention.

The inventive particles' shell material has an environmental biodegradability greater than 50% as measured by the OECD 301D method that utilizes biological oxygen demand as the criteria for measuring degradability. Conventional capsules utilize polymers that may be biodegradable prior to shell formation, but due to the nature of crosslinkers that are used and the chemical structure of the final crosslinked polymer, microbes are no longer able to attach to the polymer or the backbone to sufficiently degrade the shell material. The inventive particles utilize monomers and polymers that retain degradable functional groups even after the crosslinking is complete, such that microbes in the environment are able to digest the shell material.

In order to deliver a noticeable benefit to the consumer, yet deliver that benefit at a low cost, encapsulation is used to isolate a uniquely different fragrance or flavor active from the non-encapsulated fragrance or flavor that is incorporated into the formulation. Acclamation to a flavor or fragrance requires a much higher concentration of the same fragrance or flavor to achieve noticeability. The invention allows one to encapsulate a uniquely different fragrance or flavor to incorporate into the composition, and achieve noticeability at significantly lower concentrations of the encapsulated active. Improvement of retention of capsules onto the fabric during rinse-off processes also has the potential to reduce cost.

Particles

The invention addresses one or more of the prior art deficiencies described above by providing controlled release particles. The particles are particularly well-suited for use in encapsulation of hydrophobic, nonpolar materials.

The particles are preferably used in a consumer product composition, such as, e.g., a cleaning composition, a fabric care composition and/or a personal care composition.

The controlled release particles of the present invention comprise a core and a shell. The core comprises at least one hydrophobic active ingredient, optionally a sugar alcohol, optionally a plasticizer. The shell comprises a reaction product of at least an isocyanate resin, at least an epoxy resin, at least a glycidyloxy-alkyl-trialkoxy siloxane, with at least a treated protein isolate, at least an amino acid isocyanate adduct, at least an amino acid epoxide adduct, optionally an amino polysaccharide, optionally a tetrahydroxy ortho siloxane, treated or gelatinized polysaccharide.

The particles generally comprise a polyurea shell that is a reaction product of an isocyanate and/or an epoxy with a treated protein isolate and/or polysaccharide. The amino acid adducts of the invention are surface active monomers that seal the pores of the microcapsule shell as well as facilitate dispersion stability of the microcapsules in the surrounding medium. In addition, treated protein isolate results in better solubility and dispersibility in water in addition to enhancing the number of reactive moieties—both of these attributes reduce the permeability of the formed membrane.

In certain embodiments, the amino acid adduct comprises at least one functional group that is capable of reacting with isocyanate and or epoxy functional groups.

In certain embodiments, the amino acid isocyanate adduct comprises amine-acid functionalities and is a reaction product of an amino acid comprising least 2 reactive amines with a diisocyanate, wherein the diisocyanate is used at a molar stoichiometric ratio of isocyanate functionality:amine functionality of 1:2. Such amino acid isocyanate adduct has reactive primary and/or secondary amine, and carboxylic acid reactive functionalities. The amount of amine and acid functional amino acid isocyanate adduct can be, e.g., from 0.10-5.0 wt. % more specifically 0.10 wt. % or 0.15 wt. % or 0.20 wt. % or 0.25 wt. % or 0.30 wt. % or 0.35 wt. % or 0.40 wt. % or 0.45 wt. % or 0.50 wt. % or 0.60 wt. % or 0.70 wt. % or 0.80 wt. % or 0.90 wt. % or 1.0 wt. % or 1.5 wt. % or 2.0 wt. % or 2.5 wt. % or 3.0 wt. % or 3.5 wt. % or 4.0 wt. % or 4.5 wt. % or 5.0 wt. %, wherein the weight percentages are based on the weight of amino acid isocyanate adduct divided by the weight of dry matter in the controlled release particle.

In certain embodiments, the amino acid epoxide adduct comprises secondary amine-hydroxy-acid functionalities that is a reaction product of an amino acid with at least one primary amine or two secondary amines and a diepoxide, wherein the epoxide is used at a stoichiometric ratio of epoxy functionalities to amine functionalities in an equivalent number ratio of 1:2. Such amino acid epoxide adduct has secondary amine, hydroxyl, and carboxylic acid reactive functionalities. The amount of amino acid epoxide adduct can be, e.g., from 0.10-5.0 wt. % more specifically 0.10 wt. % or 0.15 wt. % or 0.20 wt. % or 0.25 wt. % or 0.30 wt. % or 0.35 wt. % or 0.40 wt. % or 0.45 wt. % or 0.50 wt. % or 0.60 wt. % or 0.70 wt. % or 0.80 wt. % or 0.90 wt. % or 1.0 wt. % or 1.5 wt. % or 2.0 wt. % or 2.5 wt. % or 3.0 wt. % or 3.5 wt. % or 4.0 wt. % or 4.5 wt. % or 5.0 wt. %, wherein the weight percentages are based on the weight of amino acid epoxy adduct divided by the weight of dry matter in the controlled release particle.

The amino acid used to make the AAI adduct is preferably selected from the group consisting of lysine, arginine, ornithine, 2,4-diaminobutyric acid, lanthionine, and any amino acid or modified amino acid having two primary amines or two secondary amines or one primary amine and one secondary amine.

The diisocyanate used to synthesize AAI adduct is preferably selected from the group consisting of isophorone diisocyanate, toluene diisocyanate, hexamethylene diisocyanate, xylene diisocyanate, pentamethylene diisocyanate, 4,4'-methylene diphenyl diisocyanate, 4,4'-methylene dicyclohexyl diisocyanate, any isocyanate resin or isocyanate prepolymer having two reactive isocyanates, and mixtures thereof.

The diepoxide used to synthesize the AAE adduct is preferably selected from the group consisting of resorcinol diglycidyl ether, bisphenol-A diglycidyl ether, bisphenol-F diglycidyl ether, hydrogenated bisphenol-A diglycidyl ether, any epoxy resin or epoxy prepolymer having two reactive glycidyl ether and mixtures thereof.

The amino acid to synthesize the AAE adduct is preferably any amino acid or modified amino acid having one primary amine ($NH_2$) or two secondary amines (NH), wherein the $NH_2$ or NH is chemically bonded to carbon(s) that is/are separated from the carbonyl carbon of the carboxylic acid of the amino acid by at least one carbon (the alpha-carbon). More preferably, said amino acid is beta-alanine or beta-leucine.

In a preferred embodiment, the AAI adduct is a reaction product of lysine with isophorone diisocyanate or toluene diisocyanate.

In a preferred embodiment, the AAE epoxide adduct is a reaction product of beta alanine with resorcinol diglycidyl ether.

In certain embodiments, the protein isolate comprises a material selected from the group consisting of proteinogenic L-amino acids, animal or plant proteins, animal or plant protein hydrolysates, animal or plant proteins produced by physicochemical or fermentative or enzymatic treatment. Animal based proteins comprise those derived from meat (mammals, birds, reptiles, amphibians, fish), crabs, crustaceans, mussels, mollusks, insects, eggs, milk, casein, whey, gelatin, algae and mixtures thereof. Plant based proteins comprise those derived from cereals such as wheat, barley, rye, spelt gluten, rapeseed, sunflower, rice, potato, corn, soybean, bean, pea, mung, chickpea, lentil, lupin, alfalfa, hemp, and mixtures thereof.

The treated protein isolate is present in active material loaded particles of the invention in an amount effective to improve the barrier properties and environmental biodegradability of the membrane. The treated protein isolate is preferably made via controlled hydrolysis of the protein isolate to achieve a solution or nano-dispersion of the poorly water soluble protein. The hydrolysis of the protein isolate also results in an increase in the number of reactive moieties in protein isolate. The amount of treated protein isolate can be, e.g., from 15-45 wt. % more specifically 15 wt. % or 20 wt. % or 25 wt. % to 30 wt. % or 31 wt. % or 32 wt. % or 33 wt. % or 34 wt. % or 35 wt. % or 36 wt. % 37 or wt. % 38 or wt. % 39 or wt. % or 40 wt. % or 41 wt. % or 42 wt. % or 43.wt % or 44 wt. % or 45 wt. %, wherein the weight percentages are based on the weight of protein isolate divided by the weight of dry matter in the controlled release particle.

In certain embodiments, the polysaccharide comprises a member selected from the group consisting of natural starches such as tapioca, potato, corn, rice, wheat; modified starches such as carboxy modified polysaccharide or cellulose such as carboxymethyl starch, carboxymethyl chitosan, amino polysaccharide (chitosan), chitosan oligosaccharide, hydroxy propyl methyl starch, hydroxy propyl cellulose, ethyl cellulose, methyl cellulose; waxy maize starches; pre-gelatinized starches; pregelatinized polysaccharides, pre-gelatinized waxy maize starches; octenyl succinic anhydride modified starch; anionically modified starches; cationically modified starches; and mixtures thereof.

The amino polysaccharide (e.g, chitosan) is present in active loaded particles of the invention in an amount effective to form i) coacervate layer by interacting with carboxylic functionality available on capsule membrane, ii) improve the environmental biodegradability of the particles and iii) enhance the deposition efficiency of capsules on substrates. The amount of amino polysaccharide can be, e.g., from 0.05-4.0 wt. % more specifically 0.05 wt. % or 0.1 wt. % or 0.15 wt. % or 0.20 wt. % or 0.25 wt. % or 0.50 wt. % or 0.75 wt. % to 1.0 wt. % or 1.15 wt. % or 1.30 wt. % or 1.40 wt. % or 1.50 wt. % or 1.60 wt. % or 1.70 wt. % or 1.8 wt. % or 1.9 wt. % or 1.95 wt. % or 2.25 wt. % or 2.5 wt. % 2.75 wt. % or 3.0 wt. % or 3.5 wt. % or 4.0 wt. %, wherein the weight percentages are based on the weight of amino polysaccharide divided by the weight of dry matter in the controlled release particle.

The gelatinized polysaccharide (e.g., gelatinized starch or gelatinized polysaccharide) is present in active loaded particles of the invention in an amount effective to improve the deposition efficiency of capsules on substrates. The addition of this special polysaccharide may also enhance the biodegradability of membrane. The amount of special polysaccharide can be, e.g., from 0.05-4.5 wt. % more specifically 0.05 wt. % or 0.10 wt. % or 0.15 wt. % or 0.20 wt. % or 0.25 wt. % or 0.30 wt. % or 0.35 wt. % 0.40 wt. % or 0.45 wt. % or 0.5 wt. % or 0.75 wt. % or 0.95 wt. % or 1.0 wt. % 1.5 wt. % 1.75 wt. % or 2.0 wt. % or 2.5 wt. % or 2.75 wt. % or 3.0 wt. % or 3.25 wt. % or 3.50 wt. % 3.55 wt. % or 3.75 wt. % 4.0 wt. % or 4.25 wt. % or 4.5 wt. %, wherein the weight percentages are based on the weight of treated polysaccharide divided by the weight of dry matter in the controlled release particle.

In certain embodiments, the organofunctional silane comprises a material selected from the group consisting of alkoxylated silanes, trialkoxy silanes, functionalized trialkoxysilanes, tetraalkoxyated silanes, 1,2 bis(triethoxysilyl) ethane and glycidyl ether silanes.

In certain embodiments, the organofunctional silane as at least one member selected from the group consisting of alkoxylated silane, trialkoxy silanes, functionalized trialkoxysilanes (amino, glycidoxy, methacryloxy, vinyl), tetraalkoxylated silanes including tetramethoxy silane and tetraethoxy silane, 1,2-bis(triethoxysilyl)ethane, glycidoxyalkyltrialkoxy silanes such as glycidoxypropyltrimethoxysilane, glycidoxypropyltriethoxysilane, glycidoxyoctyltrimethoxysilane; glycidoxyalkyl(alkyl)dialkoxy silanes such as glycidoxypropylmethyldimethoxy silane, glycidoxypropylmethyldiethoxy silane; and epoxyalkyltrialkoxy silanes such as epoxyhexyltrimethoxy silane.

The glycidoxy-alkyl-trialkoxy silane material is present in particles of the invention in an amount effective to improve the barrier properties and environmental biodegradability of the membrane. The amount of glycidoxy alkyl-trialkoxy silane can be, e.g., from 0.05-2.0 wt. % more specifically 0.05 wt. % or 0.10 wt. % or 0.15 wt. % or 0.2 wt. % or 0.30 wt. % or 0.40 wt. % 0.50 wt. % or 0.55 wt. % or 0.60 wt. % or 0.70 wt. % or 0.80 wt. % or 0.90 wt. % 1.0 wt. % or 1.25 wt. % or 1.50 wt. % or 1.75 wt. % or 2.0 wt. %, wherein the weight percentages are based on the weight of silane divided by the weight of dry matter in the controlled release particle.

The tetrahydroxy orthosiloxane (freshly prepared from tetraalkoxy orthosiloxane by acidic hydrolysis in water followed by removal of alcohol) material (as silicate) is present in particles of the invention in an amount effective to improve the barrier properties and environmental biodegradability of the membrane. The amount of glycidoxy alkyl-trialkoxy silane can be, e.g., from 0.05-4.0 wt. % more specifically 0.05 wt. % or 0.10 wt. % or 0.15 wt. % or 0.20 wt. % or 0.25 wt. % or 0.50 wt. % or 0.75 wt. % 1.0 wt. % or 1.25 wt. % or 1.50 wt. % or 1.75 wt. % or 1.85 wt. % or 2.0 wt. % 2.5 wt. % or 2.75 wt. % or 3.0 wt. % or 3.25 wt. % or 3.50 wt. % or 3.75 wt. % or 4.0 wt. %, wherein the weight percentages are based on the weight of silane divided by the weight of dry matter in the controlled release particle.

In certain embodiments, the isocyanate that reacts to form the shell material of the controlled release particles comprises a member selected from the group consisting of an aliphatic isocyanate, an aromatic isocyanate, a polymeric isocyanate, a cyclic isocyanate, a hydrophilic isocyanate, a hydrophobic isocyanate, a isocyanurate, a waterborne isocyanate and a urethane acrylate containing isocyanate functionalities.

In certain embodiments, the isocyanate comprises aliphatic isocyanates, aromatic isocyanates, polymeric isocyanates, cyclic isocyanates, hydrophilic isocyanates, hydrophobic isocyanates, waterborne isocyanates. Exemplary isocyanates are selected from the group consisting of hexamethylene diisocyanates (Desmodur H, Desmodur N3600, Desmodur N3800, Desmodur N3900, Desmodur N3200, Desmodur N3200A, Desmodur N3300, Desmodur N3400, Takenate D-170N), hexamethylene diisocyanate buret, isophorone diisocyanates (Desmodur XP2565, Desmodur Z4470), blends of hexamethylene diisocyanate and isophorone diisocyanate (Desmodur XP2847, Desmodur XP2489, Desmodur XP2838, Desmodur XP2763), pentane-1,5-diisocyanate (Stabio D-370N, Stabio D-376N), xylylene diisocyanate (Takenate 500, Takenate 600, Takenate D-110N, Takenate D-131N), polymeric methylene diphenyl diisocyanate (Mondur MR Lite), polymeric MDI (Desmodur VK 5, Desmodur VL R10, Desmodur 44V40L, Desmodur 44V70L), polyether modified hydrophilic polyisocyanates (Bayhydur XP2451/1, Bayhydur XP2547, Bayhydur XP2759, Bayhydur Ultra 304, Bayhydur Ultra 2487/1), CN9302, ionically modified isocyanates (Bayhydur 2858 XP, Bayhydur XP2759, Bayhydur eco 7190), and the like.

The isocyanate utilized in the reaction to make the shell of the particles of the invention is an amount effective to improve the barrier properties of the membrane. The amount of isocyanate can be, e.g., from 1.5-15 wt. % more specifically 1.5 wt. % or 2.0 wt. % or 2.5 wt. % or 3.0 wt. % or 3.5 wt. % or 4.0 wt. % to 4.5 wt. % or 4.75 wt. % or 5.0 wt. % or 5.25 wt. % or 5.50 wt. % or 6.0 wt. % or 6.25 wt. % or 6.5 wt. % or 6.75 wt. % or 7.0 wt. % 7.25 or 7.50 wt. % or 7.75 wt. % or 8.0 wt. % or 8.5 wt. % or 9.0 wt. % or 9.5 wt. % or 10.0 wt. % or 11.0 wt. % or 12.0 wt. % or 13.0 wt. % or 14.0 wt. % or 15.0 wt. %, wherein the weight percentages are based on the weight of isocyanate divided by the weight of dry matter in the controlled release particle.

In certain embodiments, the epoxy that reacts to form the shell material of the controlled release particles comprises a member selected from the group consisting of an epoxidized unsaturated oil, an epoxidized vegetable oil, an epoxidized alcohol, an epoxidized silane, an epoxidized polysaccharide, a trimethylol propane triglycidyl ether, tetraglycidyl ether sorbitol, multi glycidyl ether of phenol novolac, resin containing acrylate and epoxy functional groups, a diepoxide of a cycloaliphatic alcohol, a hydrogenated Bisphenol A, and a resorcinol/bisphenol F resin with polyfunctional epoxide resin blend, low temperature curing agents having 2 or more epoxy functional groups which are terminally located. Suitable materials include trimethylol propane triglycidyl ether, diglycidoxy of ethylene glycol, diglycidoxy of polyethylene glycol, diglycidoxy of propylene glycol, diglycidoxy of polypropylene glycol, N,N,O-triglycidyl aminophenol, N,N,N,N-tetraglycidyl of diaminodiphenylmethane, resins containing acrylate and epoxy functional groups, diglycidoxy of the cycloapliphatic alcohol, polyglycidoxy of polyol, hydrogenated Bisphenol A, resorcinol/bisphenol F resin with polyfunctional epoxide resin blend, and perfume soluble any diglycidyl and or diglycidoxy moiety containing resins, and perfume soluble any polyglycidyl or polyglycidoxy comprising resin.

The epoxy utilized in the reaction to make the shell of the particles of the invention is an amount effective to improve the barrier properties of the membrane. The amount of epoxy can be, e.g., from 0.25-10.0 wt. % more specifically 0.25 wt. % or 0.50 wt. % or 0.75 wt. % or 1.0 wt. % or 1.25 wt. % or 1.50 wt. % or 1.60 wt. % or 1.75 wt. % or 2.0 wt. % or 2.5 wt. % or 3.0 wt. % or 3.5 wt. % or 4.0 wt. % or 4.5 wt. % 5.0 wt. % or 6 wt. % or 7 wt. % or 8 wt. % or 9 wt. % or 10.0 wt. %, wherein the weight percentages are based on the weight of epoxy resin divided by the weight of dry matter in the controlled release particle.

The active ingredient needing to be encapsulated is a hydrophobic or water insoluble substance that is active (or effective) to provide a desired effect, alone or in combination with other substances and/or conditions. It is present in the particles in an amount effective to provide a desired effect. The amount can be, e.g., from 30-80.0 wt. % more specifically 30 wt. % or 35.0 wt. % or 40 wt. % or 45 wt. % or 50 wt. % or 53.0 wt. % or 55 wt. % or 60 wt. % or 65 wt. % or 70 wt. % or 75 wt. % or 80 wt. %, wherein the weight percentages are based on the weight of hydrophobic active divided by the weight of dry matter in the composition.

The hydrophobic active ingredient is preferably a member selected from the group consisting of a flavorant, a fragrance, a chromogen, a dye, an essential oil, a sweetener, an oil, a pigment, an active pharmaceutical ingredient, a moldicide, a herbicide, a fertilizer, a pheromone, phase change material, an adhesive, a vitamin oil, a vegetable oil, a triglyceride and a hydrocarbon.

Suitable flavorants include but are not limited to oils derived from plants and fruits such as citrus oils, fruit essences, peppermint oil, clove oil, oil of wintergreen, anise, lemon oil, apple essence, and the like. Artificial flavoring components are also contemplated. Those skilled in the art will recognize that natural and artificial flavoring agents may be combined in any sensorially acceptable blend. All such flavors and flavor blends are contemplated by this invention. Carriers may also be mixed with flavors to reduce the intensity, or better solubilize the materials. Carriers such as vegetable oils, hydrogenated oils, triethyl citrate, and the like are also contemplated by the invention.

Suitable fragrances include but are not limited to compositions comprising materials having an Log P (logarithm of octanol-water partition coefficient) of from about 2 to about 12, from about 2.5 to about 8, or even from about 2.5 to about 6 and a boiling point of less than about 280° C., from about 50° C. to about less than about 280° C., from about 50° C. to about less than about 265° C., or even from about 80° C. to about less than about 250° C.; and optionally, an ODT (odor detection threshold) of less than about 100 ppb, from about 0.00001 ppb to about less than about 100 ppb, from about 0.00001 ppb to about less than about 50 ppb or even from about 0.00001 ppb to about less than about 20 ppb. Diluents that are miscible in the fragrance oil, and act to reduce the volatility of the fragrance oil, such as isopropyl myristate, iso E super, triethyl citrate, vegetable oils, hydrogenated oils, neobee, and the like are also contemplated by the invention.

Suitable chromogens include but are not limited to Michler's hydrol, i.e. bis(p-dimethylaminophenyl)methanol, its ethers, for example the methyl ether of Michler's hydrol and the benzylether of Michler's hydrol, aromatic sulfonic and sulfinic esters of Michler's hydrol, for example the p-toluenesulfinate of Michler's hydrol, and derivatives of bis(p-dimethylaminophenyl)methylamine, e.g., N[bis(p-dimethylaminophenyl)methyl]morpholine.

Suitable dyes include but are not limited to Sudan Red 380, Sudan Blue 670, Baso Red 546, Baso Blue 688, Sudan Yellow 150, Baso Blue 645, Flexo Yellow 110, and Flexo Blue 630, all commercially available from BASF; Oil Red 235, commercially available from Passaic Color and Chemical; Morfast Yellow 101, commercially available from Morton; Nitro Fast Yellow B, commercially available from Sandoz; and Macrolex Yellow 6G, commercially available from Mobay. Preferred dyes are those having good solubility in aromatic solvents.

Suitable essential oils include but are not limited to those obtained from thyme, lemongrass, citrus, anise, clove, aniseed, roses, lavender, citronella, eucalyptus, peppermint, camphor, sandalwood, cinnamon leaf and cedar. Essential oils that exhibit antimicrobial properties are also contemplated by this invention.

Suitable sweeteners include but are not limited to materials that contain varying amounts of disaccharide and/or fructose; erythritol, honey, and/or evaporated cane juice; and rebaudioside A, and the like.

Suitable pigments include but are not limited to pearl pigments of mica group such as titanium dioxide-coated mica and colored titanium dioxide-coated mica; and pearl pigments of bismuth oxychlorides such as colored bismuth oxychloride. Such pigments are available on the market under various trade names: Flamenco series (by the Mearl Corporation), TIMIRON COLORS (by MERCK) as titanium dioxide-coated mica, Timica Luster Pigments (by MEARL). Cloisonee series (by MEARL), COLORON series (by MERCK), SPECTRA-PEARL PIGMENTS (by Mallinckrodt) as colored titanium dioxide-coated mica and MIBIRON COLORS series (by MERCK) as colored bismuth oxychloride.

Suitable active pharmaceutical ingredients include but are not limited to water insoluble materials that have a melting point below 50° C.

Suitable moldicides include but are not limited to an inorganic biocide selected from the group consisting of a metal, a metal compound and combinations thereof. Preferably, the inorganic biocide is copper, cobalt, boron, cadmium, nickel, tin, silver, zinc, lead bismuth, chromium and arsenic and compounds thereof. More preferably, the copper compound is selected from the group consisting of copper hydroxide, cupric oxide, cuprous oxide, copper carbonate, basic copper carbonate, copper oxychloride, copper 8-hydroxyquinolate, copper dimethyldithiocarbamate, copper omadine and copper borate. Suitable moldicides further include but are not limited to fungicidal compounds such as, e.g., isothiazolone compounds. Typical examples of isothiazolone compounds include but not limited to: methylisothiazolinone; 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 2-ethyl-4-isothiazoline-3-one, 4,5-dichloro-2-cyclohexyl-4-isothiazoline-3-one, 5-chloro-2-ethyl-4-isothiazoline-3-one, 2-octyl-3-isothiazolone, 5-chloro-2-t-octyl-4-isothiazoline-3-one, 1,2-benzisothiazoline-3-one, preferably 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, etc., more preferably 5-chloro-2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, chloromethyl-isothiazolinone, 4,5-Dichloro-2-n-octyl-3(2H)-isothiazolone and 1,2-benzisothiazolin-3-one.

Suitable herbicides include but are not limited to 2-(2-chloro-4-methylsulfonylbenzoyl)-1,3-cyclohexanedione, 2-(2-nitrobenzoyl)-4,4-dimethyl-1,3-cyclohexanedione, 2-(2-(nitrobenzoyl)-5,5-dimethyl-1,3-cyclohexanedione, and their 2-benzoylcyclohexanedione derivatives, in addition to those listed in WO2006024411A2.

Suitable phase change materials include but are not limited to a crystalline alkyl hydrocarbon which is comprised of one or more crystalline straight chain alkyl hydrocarbons having 14 or more carbon atoms and heats of fusion greater than 30 cal/g. The melting and freezing point of the alkyl hydrocarbon is in the range of 0° to 80° C., preferably 5° to 50° C., and most preferably, 18° to 33° C. Representative materials are crystalline polyolefins such as polyethylene, polypropylene, polybutene, crystalline polystyrene, crystalline chlorinated polyethylene and poly(4-methylpentene-1). Crystalline ethylene copolymers such as ethylene vinylacetate, crystalline ethylene acrylate copolymers, ionomers, crystalline ethylene-butene-1 copolymers and crystalline ethylene-propylene copolymers are also useful polyolefins.

Preferably, the polyolefins are crosslinked such that they are form stable upon heating above their crystalline melting point.

Suitable adhesives include but are not limited to compositions comprising an elastomer and a tackifying agent. The elastomer adds toughness to the adhesive film and also is responsible for at least part of the required initial pressure-sensitive tackiness. The elastomeric materials are water insoluble and are inherently tacky or are capable of being rendered tacky by mixture with compatible tackifying resins. Preferably the elastomers are natural rubber or butadiene or isoprene synthetic polymers or copolymers such as butadiene-isobutylene copolymers, butadiene-acrylonitrile copolymers, butadiene-styrene copolymers, polychloroprene or similar elastomers. A combination of the above elastomers may be utilized. Preferred tackifying agents include unsaturated natural resins such as rosin or derivatives thereof, such as rosin esters of polyols such as glycerol or pentaerythritol, hydrogenated rosins or dehydrogenated rosins Suitable vitamin oils include but are not limited to fat-soluble vitamin-active materials, pro vitamins and pure or substantially pure vitamins, both natural and synthetic, or chemical derivatives thereof, crude extractions containing such substances, vitamin A, vitamin D, and vitamin E active materials as well as vitamin K, carotene and the like, or mixtures of such materials. The oil-soluble vitamin oil concentrate may be a high potency fish liver oil containing vitamin A and/or D, a synthetic vitamin A palmitate and/or acetate concentrated in an oil solution, vitamin D, or D either concentrated in oil solution or as an oleaginous resin, vitamin E (d-alpha tocopheryl acetate) in an oil solution, or vitamin K in oil solution, or beta-carotene as a crystalline oil suspension in oil.

Suitable vegetable oils include but are not limited to oils derived from palm, corn, canola, sunflower, safflower, rapeseed, castor, olive, soybean, coconut and the like in both the unsaturated forms and hydrogenated forms, and mixtures thereof.

Suitable triglycerides include but are not limited to those disclosed in U.S. Pat. No. 6,248,909B1.

Suitable hydrocarbons that can be the active or can be used in combination with the active in order to change the physical or chemical properties of the active, include but are not limited to, waxes, density modifiers, surface tension modifiers, melting point modifiers, viscosity modifiers, and mixtures thereof. Examples include animal waxes such as beeswax, plant waxes such as carnauba wax, candelilla wax, bayberry wax, castor wax, tallow tree wax, soya wax, rice bran wax, hydrogenated rice bran wax, soya wax, hydrogenated soya wax, hydrogenated vegetable oil. Examples of petroleum derived waxes are paraffin waxes and microcrystalline waxes. An example of synthetic wax is polyethylene wax. Examples of materials that can modify the density of the active phase in the particle are brominated vegetable oil, nanoclays such as montmorrilonite or kaolin, hydrophobically modified clays, hydrophobically modified precipitated silicas or fumed silicas. Examples of oil thickening agents are waxes mentioned above, modified organopolysiloxanes, silicone gums, hydrogenated castor oil, paraffin oils, polyolefins, and the like.

In certain embodiments, a plasticizer is included in the oil phase and is at least one member selected from the group consisting of methyl esters of rosin, polyazelate esters, di-fatty acid esters, citrate esters, polyadipate esters and polyester resins consisting of inner and intra-esters of polyhydroxy carboxylic acids.

The amount of plasticizer can be, e.g., from 0.05-2.0 wt. %, more specifically 0.05 wt. % or 0.1 wt. % or 0.15 wt. % or 0.20 wt. % or 0.25 wt. % or 0.35 wt. % or 0.40 wt. % or 0.45 wt. % or 0.50 wt. % or 0.55 wt. % or 0.60 wt. % or 0.65 wt. % or 0.70 wt. % or 0.75 wt. % or 0.80 wt. % or 0.90 wt. % or 1.0 wt. % or 1.25 wt. % or 1.50 wt. % or 1.75 wt. % or 2.0 wt. %, wherein the weight percentages are based on the weight of plasticizer divided by the weight of dry matter in the controlled release particle.

In certain embodiments, a sugar alcohol is included in the oil phase and is at least one member selected from the group consisting of mono saccharide, disaccharide, trisaccharide, tetrasaccharide and pentasaccharide.

The sugar alcohol is present in particles of the invention in an amount effective to improve the barrier properties of the membrane. The amount of sugar alcohol can be, e.g., from 0.05-2.0 wt. % more specifically 0.05 wt. % or 0.10 wt. % or 0.15 wt. % or 0.20 wt. % or 0.25 wt. % or 0.50 wt. % or 0.75 wt. % 1.0 wt. % or 1.25 wt. % or 1.50 wt. % or 1.75 wt. % or 2.0 wt. %, wherein the weight percentages are based on the weight of sugar alcohol divided by the weight of dry matter in the controlled release particle.

Cationic particles have a higher probability of adhering to anionic fabric in the laundering environment. Amine-functionality containing materials that can be incorporated into the spray-ready emulsion, which may have a favorable effect on adhesion of particles onto skin, hair, or fabric substrates comprise a polymer selected from the group consisting of polysaccharides, in one aspect, cationically modified starch and/or cationically modified guar; polysiloxanes; poly diallyl dimethyl ammonium halides; copolymers of poly diallyl dimethyl ammonium chloride and polyvinyl pyrrolidone; a composition comprising polyethylene glycol and polyvinyl pyrrolidone; acrylamides; imidazoles; imidazolinium halides; polyvinyl amine; copolymers of poly vinyl amine and N-vinyl formamide; polyvinylformamide, copolymers of polyvinylamine and polvyinylalcohol oligimers of amines, in one aspect a diethylenetriamine, ethylene diamine, bis(3-aminopropyl)piperazine, N,N-Bis-(3-aminopropyl) methylamine, tris(2-aminoethyl)amine and mixtures thereof; polyethyleneimime, a derivatized polyethyleneimine, in one aspect an ethoxylated polyethyleneimine; diester quaternary ammonium surfactants such as methyl bis-[ethyl(coconut)]-2-hydroxyethyl ammonium methyl sulfate, methyl bis-[ethyl(decyl)]-2-hydroxyethyl ammonium methyl sulfate, methyl bis-[ethyl(dodeceyl)]-2-hydroxyethyl ammonium methyl sulfate, methyl bis-[ethyl(lauryl)]-2-hydroxyethyl ammonium methyl sulfate, methyl bis-[ethyl(palmityl)]-2-hydroxyethyl ammonium methyl sulfate, methyl bis-[ethyl(soft-tallow)]-2-hydroxyethyl ammonium methyl sulfate, and the like; diester quat combined with laminate nanoclays such as laponite, bentonite, montmorillonite, and the like; chitosan with various degrees of deacetylation, carboxymethyl chitosans, glycol chitosans, whey protein, sodium caseinate, silk protein, 1H-Imidazolium, 1-ethenyl-3-methyl-, chloride, polymer with 1-ethenyl-2-pyrrolidinone, polyamines, polysaccharides with cationic modification, and mixtures thereof. Polysaccharides can be employed with cationic modification and alkoxy-cationic modifications, such as cationic hydroxyethyl, cationic hydroxy propyl. For example, cationic reagents of choice are 3-chloro-2-hydroxypropyl trimethylammonium chloride or its epoxy version. Furthermore, up to 5 different types of functional groups may be attached to the polysaccharides. Also, polymer graft chains may be differently modified than the backbone. The counterions can be any halide ion or organic counter ion. The preferred cationic starch has a molecular weight of from about 100,000 to about 500,000,000, preferably from about 200,000 to about 10,000,000 and most preferably from about 250,000 to about 5,000,000. The preferred cationic starch products are HI-CAT CWS42 and HI-CAT 02 and are commercially available from ROQUETTE AMERICA, Inc. The preferred cationic guar has a molecular weight of from about 50,000 to about 5,000,000. The preferred cationic guar products are Jaguar C-162 and Jaguar C-17 and are commercially available from Rhodia Inc.

The cationically modified materials in the controlled release particles are present, in an amount on a dry basis (weight of cationically modified material per weight of dry matter in the suspension) from 0.01 to 3 wt. %, more specifically 0.01 wt. % or 0.02 wt. % or 0.03 wt. % or 0.04 wt. % or 0.05 wt. % or 0.06 wt. % or 0.07 wt. % or 0.08 wt. % or 0.09 wt. % 0.1 wt. % or 0.15 wt. % or 0.20 wt. % 0.25 wt. % or 0.30 wt. % or 0.35 wt. % or 0.40 wt. % or 0.45 wt. % or 0.50 wt. % or 1 wt. % or 1.25 wt. % or 1.5 wt. % or 1.75 wt. % or 2.0 wt. % or 2.25 wt. % or 2.25 wt. % or 2.5 wt. % or 2.75 wt. % or 3.0 wt. %; wherein the weight percentages are based on the weight of cationically modified materials divided by the weight of dry matter in the controlled release particle.

The controlled release particles are preferably spherical but non-spherical shapes are also within the scope of the invention. The particles preferably have a diameter from 0.05-250 microns, or from 0.1 microns to less than 100 microns.

Method of Making the Particles

The controlled release particles of the invention preferably comprise a core and a polymeric shell, wherein the core comprises: (i) at least one hydrophobic active ingredient; and (ii) the polymeric shell is obtained by an interfacial polymerization reaction facilitated by the reaction among an isocyanate resin, an epoxy resin, a treated protein isolate, an AAI adduct and/or an AAE adduct, glycidyloxyalkyltrailkoxy silane, sugar alcohol, tetrahydroxy orthoxiloxane, amino polysaccharide, treated polysaccharide (e.g., gelatinized starch).

Not to be limited by theory, polyurea capsules are made via interfacial polymerization achieves a shell at the oil-water interface via a chemical reaction between reactive prepolymers and/or monomers dissolved or dispersed in the oil phase with reactive monomers and/or prepolymers dissolved or dispersed in the aqueous phase. The choice of monomers or prepolymers or resins, crosslinking conditions, and emulsifiers used influences the permeability properties of the membrane.

Not to be limited by theory, the treated protein isolate, amino acid adducts, tetrahydroxy orthosiloxane, amino polysaccharide added in the aqueous phase can react with several functional groups present in the hydrophobic oil phase, including isocyanate, epoxy, epoxy silanes, and organofunctional silane. The reactivity of amine is higher with isocyanate, and therefore provides a membrane via an interfacial polymerization reaction that limits the diffusion of the hydrophobic active into the surrounding aqueous phase. Not to be limited by theory, the amine moieties of treated protein isolate, and amino acid adducts can also react with epoxy functionality to form amino alcohols. The amino alcohols can in turn further react with the isocyanates, such reaction will lead to the possible formation of polyurethanes and polyureas which will reduce the permeability of the membrane. Introduction of the hydrophobic active suspended in the oil phase into the aqueous phase hydrolyzes the alkoxy silanes or alkylalkoxy silanes or glycidoxyalkyltrialkoxy silane. Hydrolysis of these organo-silanes produces hydroxy silanes, and such silanes undergo self-condensation as well as co-condensation with in-situ formed hydroxyl functional groups on the polyurea/polyurethane membrane formed by interfacial polymerization. Such condensation forms an interlinked silicate layer with the polyurea/polyurethane membrane that in turn strengthens the membrane and reduces permeability of the membrane.

Controlled release particles of the present invention are made using the following protocol:

1) preparing a core material phase by mixing the at least one hydrophobic active material with the at least one reactive isocyanate monomer or prepolymer or resin, the at least one reactive epoxy monomer or prepolymer or resin, the optional sugar alcohol, the optional plasticizer to make a solution or dispersion; 2) making a homogeneous aqueous solution or aqueous dispersion comprising a treated protein isolate and the at least one emulsifier or surfactant; 3) adding the core material phase into the aqueous solution or dispersion to prepare an oil-in-water (O/W) emulsion at room temperature to 35° C.; 4) Continuing agitation and adjustment of pH at 35-40° C. forms capsule shell via interfacial polymerization; 5) adding aqueous solution of amine-acid functional urea linked amino acid isocyanate adduct, and amine-hydroxy-acid functional amino acid epoxide adduct into preformed capsule slurry; 6) heating the preformed capsule slurry to a temperature from 40° C. to 60° C. for further polymerization onto capsule membrane; 7) adding the freshly prepared tetrahydroxyorthosilicic acid from the hydrolysis of tetraethoxyorthosiloxane followed by removal of alcohol; 8) further adding fine powder of amino polysaccharide into slurry to form a coacervate layer onto capsule shell surface; 9) adding treated polysaccharide (gelatinized starch) dispersion into slurry; 10) optionally spray drying the capsule slurry to obtain powder version of capsule; 11) optionally, post curing the dry powder at elevated temperatures (100° C. to 150° C.) for 30 minutes to 60 minutes.

The inventors have discovered that pursuing a high degree of crosslinking in making microcapsules via chemical reaction processes that comprise interfacial polymerization via addition reactions, free radial polymerization reactions, step growth, condensation and the like, may provide a membrane with good barrier properties and mechanical properties; however, such membranes have poor environmental biodegradability. Not to be limited by theory, a high degree of crosslinking results in the absence of both functional groups and flexibility that hinders the ability of microbes to form a biofilm around the polymer membrane followed by digestion of membrane to improve biodegradability. Incorporation of biodegradable materials into the membrane via the use of protein isolate, especially treated protein isolate, polypeptides, amino polysaccharide, polysaccharides, and reactive amine-acid-hydroxyl functional moieties containing amino acid adducts, hydroxy silane can improve barrier properties of the membrane (by providing a more tortuous path for the encapsulated material to diffuse, poor miscibility of the encapsulated active material in the polymer, biodegradable polymer segments swell with water reducing the diffusion of the encapsulated active), and improved environmental biodegradability of the membrane due to the presence of amino acids, glucose units, esters, amides, peptide, and other functional groups whose breakdown is enabled by enzymes that the microbes readily secrete.

The emulsifier is present in the suspension, on a dry basis (weight of emulsifier per weight of dry matter in the suspension), of the invention in an amount effective to achieve the desired particle size distribution in oil-in-water emulsion. The amount can be, e.g., from 0.025-5 wt. % more specifically 0.025 wt. % or 0.05 wt. % 0.075 wt. % or 0.10 wt. % or 0.15 wt. % or 0.20 wt. % or 0.30 wt. % or 0.40 wt. % or 0.50 wt. % or 0.75 wt. % or 1.0 wt. % or 1.5 wt. % or 2.0 wt. % or 2.5 wt. % or 3.0 wt. % 3.5 wt. % or 4.0 wt. % or 4.5 wt. % or 5.0 wt. % or not greater than 10 wt. %.

Emulsifiers or surfactants of all types are suitable for use in the practice of the present process though it is to be appreciated, and those skilled in the art will readily recognize that different systems, e.g., different core monomer and/or core materials, will be better suited with one or more classes of emulsifiers than others. Specifically, while the present teachings are applicable to anionic, cationic, non-ionic and amphoteric emulsifiers generally, preferred emulsifiers are non-ionic emulsifiers, particularly those having polyalkylether units, alkylphenylether units especially polyethylene oxide units, with degrees of polymerization of the alkylene ether unit of greater than about 6. Preferred emulsifiers are those which significantly reduce the interfacial tension between the continuous water phase and dispersed oil phase composition, and thereby reduce the tendency for droplet coalescence. In this regard, generally the emulsifiers for use in the water phase for aiding in the oil in water emulsion or dispersion will have HLB values of from 10 to 18. Of course, emulsifiers/surfactants of lower and higher HLB values that achieve the same objective as noted are also included.

Exemplary emulsifiers include, but are not limited to gums such as acacia gum, gum arabic, konjac gum, and xantham gum; poly(meth)acrylic acids and derivatives. Most preferably, the emulsifier/emulsion stabilizer is a polyvinyl pyrrolidone, copolymers of polyvinyl pyrrolidone with vinyl acetate, vinyl alcohol, vinyl imidazole; polyglycerol oleates; polyvinyl alcohol; ethoxylate nonylphenol; secondary alcohol ethoxylate; water soluble proteins such as gelatin, whey protein, pea protein, and the like; modified polysaccharides such as octenyl succinate starch; Pickering emulsion stabilizers such as colloidal silica; and chitosan.

Additional exemplary anionic surfactants and classes of anionic surfactants suitable for use in the practice of the present invention include: sulfonates; sulfates; sulfosuccinates; sarcosinates; alcohol sulfates; alcohol ether sulfates; alkylaryl ether sulfates; alkylaryl sulfonates such as alkylbenzene sulfonates and alkylnaphthalene sulfonates and salts thereof; alkyl sulfonates; mono- or di-phosphate esters of polyalkoxylated alkyl alcohols or alkylphenols; mono- or di-sulfosuccinate esters of C12 to C15 alkanols orpolyalkoxylated C12 to C15 alkanols; ether carboxylates, especially alcohol ether carboxylates; phenolic ether carboxylates; polybasic acid esters of ethoxylated polyoxyalkylene glycols consisting of oxybutylene or the residue of tetrahydrofuran; sutfoalkylamides and salts thereof such as N-methyl-N-oleoyltaurate Na salt; polyoxyalkylene alkylphenol carboxylates; polyoxyalkylene alcohol carboxylates alkyl polyglycosidelalkenyl succinic anhydride condensation products; alkyl ester sulfates; naphthalene sulfonates; naphthalene formaldehyde condensates; alkyl sulfonamides; sulfonated aliphatic polyesters; sulfate esters of styrylphenyl alkoxylates; and sulfonate esters of styrylphenyl alkoxylates and their corresponding sodium, potassium, calcium, magnesium, zinc, ammonium, alkylammonium, diethanolammonium, or triethanolammonium salts; salts of ligninsulfonic acid such as the sodium, potassium, magnesium, calcium or ammonium salt; polyarylphenol polyalkoxyether sulfates and polyarylphenol polyalkoxyether phosphates; and sulfated alkyl phenol ethoxylates and phosphated alkyl phenol ethoxylates; sodium lauryl sulfate; sodium laureth sulfate; ammonium lauryl sulfate; ammonium laureth sulfate; sodium methyl cocoyl taurate; sodium lauroyl sarcosinate; sodium cocoyl sarcosinate; potassium coco hydrolyzed collagen; TEA (triethanolamine) lauryl sulfate; TEA (Triethanolamine) laureth sulfate; lauryl or cocoyl sarcosine; disodium oleamide sulfosuccinate; disodium laureth sulfosuccinate; disodium dioctyl sulfosuccinate; N-methyl-N-oleoyltaurate Na salt; tristyrylphenol sulphate; ethoxylated lignin sulfonate; ethoxylated nonylphenol phosphate ester calcium alkylbenzene sulfonate; ethoxylated tridecylalcohol phosphate ester, dialkyl sulfosuccinates; perfluoro (C6-C18)alkyl phosphonic acids; perfluoro(C6-C18)alkyl-phosphinic acids; perfluoro(C3-C20)alkyl esters of carboxylic acids; alkenyl succinic acid diglucamides; alkenyl succinic acid alkoxylates; sodium dialkyl sulfosuccinates; and alkenyl succinic acid alkylpolyglykosides. Further exemplification of suitable anionic emulsifiers include, but are not limited to, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesuifonate, sodium dialkylsulfosuccinates, dioctyl sulfosuccinate, sodium dilaurylsulfosuccinate, poly(styrene sulfonate) sodium salt, alkylene-maleic anhydride copolymers such as isobutylene-maleic anhydride copolymer, or styrene-maleic anhydride copolymers, or ethylene maleic anhydride copolymer gum arabic, sodium alginate, carboxymethylcellulose, cellulose sulfate and pectin, poly(styrene sulfonate), pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; maleic anhydride copolymers (including hydrolyzates thereof), polyacrylic acid, polymethacrylic acid, acrylic acid alkyl acrylate copolymers such as acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

Exemplary amphoteric and cationic emulsifiers include alkylpolyglycosides; betaines; sulfobetaines; glycinates; alkanol amides of C8 to C18 fatty acids and C8 to C18 fatty amine polyalkoxylates; C1 to C18 alkyldimethylbenzylammonium chlorides; coconut alkyldimethylaminoacetic acids: phosphate esters of C8 to C18 fatty amine polyalkoxylates; alkylpolyglycosides (APG) obtainable from an acid-catalyzed Fischer reaction of starch or glucose syrups with fatty alcohols, in particular C8 to C18 alcohols, especially the C8 to C10 and C12 to C14 alkylpolyglycosides having a degree of polymerization of 1.3 to 1.6, in particular 1.4 or 1.5. Additional cationic emulsifiers include quaternary ammonium compounds with a long-chain aliphatic radical, e.g. distearyldiammonium chloride, and fatty amines. Among the cationic emulsifiers which may be mentioned are alkyldimethylbenzylammonium halides, alkyldimethylethyl ammonium halides, etc. specific cationic emulsifiers include palmitamidopropyl trimonium chloride, distearyl dimonium chloride, cetyltrimethylammonium chloride, 1H-Imidazolium, 1-ethenyl-3-methyl-, chloride, polymer with 1-ethenyl-2-pyrrolidinone, and polyethyleneimine. Additional amphoteric emulsifiers include alkylaminoalkane carboxylic acids betaines, sulphobetaines, imidazoline derivatives, lauroamphoglycinate, sodium cocoaminopropionate, and the zwitterionic emulsifier cocoamidopropyl betaine.

Suitable non-ionic emulsifiers are characterized as having at least one non-ionic hydrophilic functional group. Preferred non-ionic hydrophilic functional groups are alcohols and amides and combinations thereof. Examples of non-ionic emulsifiers include: mono and diglycerides; polyarylphenol polyethoxy ethers; polyalkylphenol polyethoxy ethers; polyglycol ether derivatives of saturated fatty acids; polyglycol ether derivatives of unsaturated fatty acids; polyglycol ether derivatives of aliphatic alcohols; polyglycol ether derivatives of cycloaliphatic alcohols; fatty acid esters of polyoxyethylene sorbitan; alkoxylated vegetable oils; alkoxylated acetylenic diols; polyalkoxylated alkylphenols; fatty acid alkoxylates; sorbitan alkoxylates; sorbitol esters; C8 to C22 alkyl or alkenyl polyglycosides; polyalkoxy styrylaryl ethers; amine oxides especially alkylamine oxides; block copolymer ethers; polyalkoxylated fatty glyceride; polyalkylene glycol ethers; linear aliphatic or aromatic polyesters; organo silicones; sorbitol ester alkoxylates; ethoxylated castor oil; amides of fatty acids such as stearamide, lauramide diethanolamide, and lauramide monoethanolamide; aryl ethers of polyoxyalkylene glycols such as polyoxyethylene glycol nonylphenyl ether and polypropylene glycol stearyl ether. Also preferred as non-ionic emulsifiers are various latex materials, stearates, and lecithins.

Further exemplary emulsifiers that are available in anionic, nonionic, and cationic forms are colloidal silica suspensions that comprise a suspension of silica particles having a particle size from about 8 nanometers to 40 nanometers. Laponite and bentonite clays can also be exfoliated to nanometer size using high shear to make suspensions in water. Such inorganic solid particle suspensions can be used as emulsifiers to make Pickering oil-in-water emulsions.

In a preferred embodiment of the invention, the aqueous suspension of controlled release particles is dried into a powder. Spray drying is an economical process that can be used to dehydrate the slurry. Spray drying of the particle suspension is preferably conducted in a co-current spray dryer, at an inlet air temperature of 325 to 415° F. (163-213° C.), preferably from 355 to 385° F. (179-196° C.) and an outlet air temperature of 160 to 215° F. (71-101° C.), preferably from 175-195° F. (79-91° C.). Dry powder manufactured via spray drying is readily redispersed back into water, without the formation of aggregates, due to the presence of surface active amino acid adducts on the surface of the microcapsules.

Compositions Containing the Particles

The invention further comprises compositions (e.g., products, articles of manufacture, etc.) comprising the controlled release particles. Such compositions include but are not limited baby care, beauty care, fabric & home care, family care, feminine care, health care, snack and/or beverage products or devices intended to be used or consumed in the form as sold, and not intended for subsequent commercial manufacture or modification. Such products include but are not limited to fine fragrances (e.g., perfumes, colognes eau de toilettes, after-shave lotions, pre-shave, face waters, tonics, and other fragrance-containing compositions for application directly to the skin), diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee. Moreover, such products include, but are not limited to, a powdered food product, a fluid food product, a powdered nutritional supplement, a fluid nutritional supplement, a fluid fabric enhancer, a solid fabric enhancer, a fluid shampoo, a solid shampoo, hair conditioner, body wash, solid antiperspirant, fluid antiperspirant, solid deodorant, fluid deodorant, fluid detergent, solid detergent, fluid hard surface cleaner, solid hard surface cleaner, a fluid fabric refresher spray, a diaper, an air freshening product, a nutraceutical supplement, a controlled release fertilizer, a controlled release insecticide, a controlled release dye, and a unit dose detergent comprising a detergent and the controlled release particles in a water soluble film.

Fluid compositions of the invention preferably further comprise at least one suspension agent to suspend the controlled release particles, wherein the at least one suspension agent is at least one member selected from the group consisting of a rheology modifier, a structurant and a thickener. The at least one suspension agent preferably has a high shear viscosity at, 20 $sec^{-1}$ shear rate and at 21° C., of from 1 to 7000 cps and a low shear viscosity, at 0.5 $sec^{-1}$ shear rate and at 21° C., of greater than 1000 cps or 1000-200,000 cps. In certain embodiments, the composition has a high shear viscosity, at 20 $sec^{-1}$ and at 21° C., of from 50 to 3000 cps and a low shear viscosity, at 0.5 $sec^{-1}$ shear rate and at 21° C., of greater than 1000 cps or 1000-200,000 cps.

Preferably, the at least one suspension agent is selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

The invention further encompasses a slurry or dry powder comprising particles of the invention. Said slurry or dry powder may be combined with an adjunct ingredient to form a composition, for example, a consumer product.

In certain embodiments, the slurry comprises at least one processing aid selected from the group consisting of water, aggregate inhibiting materials such as divalent salts, particle suspending polymers, and mixtures thereof. Examples of aggregate inhibiting materials include salts that can have a charge shielding effect around the particle, such as, e.g., magnesium chloride, calcium chloride, magnesium bromide, magnesium sulfate and mixtures thereof. Examples of particle suspending polymers include polymers such as xanthan gum, carrageenan gum, guar gum, shellac, alginates, chitosan; cellulosic materials such as carboxymethyl cellulose, hydroxypropyl methyl cellulose and cationically charged cellulosic materials; polyacrylic acid; polyvinyl alcohol; hydrogenated castor oil; ethylene glycol distearate; and mixtures thereof.

In certain embodiments, the slurry comprises at least one carrier selected from the group consisting of polar solvents, including but not limited to, water, ethylene glycol, propylene glycol, polyethylene glycol, glycerol, non-polar solvents including but not limited to mineral oil, perfume raw materials, silicone oils, hydrocarbon paraffin oils, and mixtures thereof.

In certain embodiments, a perfume oil is combined with the slurry comprising microcapsules to provide multiple benefits. The emulsified perfume oil will increase the viscosity of the slurry and prevent the phase separation of the microcapsule particles. The mixture provides a way to deliver non-encapsulated and encapsulated fragrance from the same slurry.

In certain embodiments, the composition has at least two controlled release technologies, which release different hydrophobic oil compositions and are selected from the group consisting of neat oils, friction-triggered release microcapsules and water-triggered release microcapsules.

The invention will be illustrated in more detail with reference to the following Examples, but it should be understood that the present invention is not deemed to be limited thereto.

EXAMPLES

Materials and Methods

The following is a representative perfume oil composition used for capsule making.

TABLE 1

| Perfume oil composition | | |
|---|---|---|
| Material | wt. % | Functionality |
| CITRONELLYL NITRILE | 1.00% | NITRILE |
| TRIPLAL | 0.25% | ALDEHYDE |
| FLORHYDRAL | 0.10% | ALDEHYDE |
| ALDEHYDE C-10 | 0.10% | ALDEHYDE |
| ALDEHYDE C-12 LAURIC | 0.20% | ALDEHYDE |
| ALLYL CYCLOHEXYL PROPIONATE | 1.00% | ESTER |
| CETALOX | 0.20% | FURAN |
| ANISIC ALDEHYDE | 0.10% | ALDEHYDE |
| CYCLACET | 10.00% | ESTER |
| CYCLAPROP | 5.00% | ESTER |
| DIHYDROMYRCENOL | 10.00% | ALCOHOL |
| DIPHENYL OXIDE | 1.00% | OXIDE |
| HABANOLIDE | 2.50% | KETONE |
| YARA YARA | 2.00% | ETHER |
| CIS-3-HEXENYL SALICYLATE | 2.00% | ESTER |
| VERDOX | 2.50% | ESTER |
| HEXYLCINNAMIC ALDEHYDE | 20.00% | ALDEHYDE |
| BHT | 0.50% | 0.0025 |
| ISO E SUPER | 2.50% | KETONE |
| KOAVONE | 2.50% | 0.0625 |
| EUCALYPTOL | 0.20% | ALCOHOL |
| MANZANATE, 10% IPM | 0.50% | ESTER |
| MUSCENONE, 10% IPM | 0.50% | KETONE |

TABLE 1-continued

| Perfume oil composition | | |
|---|---|---|
| Material | wt. % | Functionality |
| LAEVO CARVONE, 10% IPM | 0.50% | 0.0025 |
| METHYL ANTHRANILATE | 0.10% | ESTER |
| METHYL IONONE GAMMA | 1.25% | KETONE |
| LILIAL | 10.00% | ALDEHYDE |
| ALDEHYDE C-12 MNA, 10% DPG | 0.50% | ALDEHYDE |
| MYRAC ALDEHYDE | 0.50% | ALDEHYDE |
| D-LIMONENE | 5.00% | TERPENE |
| PEONILE | 2.50% | NITRILE |
| ETHYLENE BRASSYLATE | 12.50% | ESTER |
| PHENOXANOL | 2.50% | ALCOHOL |

Scanning Electron Microscopy

A Phenom Pure (Nanoscience Instruments Model PW-100-019) Scanning Electron Microscope is used to understand the particle morphology, and nature of particle deposits on fabrics. PELCO tabs carbon tape (12 mm OD, Ted Pella product number 16084-1) is applied to an aluminum specimen mount (Ted Pella Product No 16111). Next, the powder sample is placed onto the carbon tape using a transfer spatula. Excess powder is removed by blowing Dust-Off compressed gas onto the sample. The stub is then left in a desiccator under vacuum for 16 hours to flash off any volatiles. The sample is then placed into the Phenom Pure, and imaged to visualize particle morphology.

Leakage Stability

A suspension of microcapsules is incorporated into Liquid Fabric Softener to deliver approximately 0.5 wt. % perfume usage level in the fabric softener. The mixture is aged 1 week at 40° C. in sealed glass jars. After aging, approximately 1.6 grams of the fabric softener mixture is diluted with 10 grams of water. 10 mL of isooctane is added to the vial, and the vial is inverted 10 times. 2-4 grams of sodium chloride is added to achieve a better separation. The sample is placed on a platform shaker for 10 minutes at 225-235 RPM agitation. After mixing, the sample is centrifuged at 2800 RPM for 2 minutes. Approximately 5 mL of the isooctane layer is removed from the vial and filtered through a 0.45 micron syringe filter. 980 microliters of this filtrate is mixed with 20 microliters of internal standard in a 2 mL GC autosampler vial. The sample is analyzed by Gas Chromatography. GC conditions are shown in Table 3 below.

TABLE 3

| GC CONDITIONS | |
|---|---|
| **Gas Chromatography/Mass Spectrophotometer Conditions** | |
| Capillary Column | DB-5MS, 30 meter, 0.25 μm film, ID = 0.25 mm |
| Carrier Gas | UHP Helium, 1.2 mL/min through the column |
| Injection Volume | 1.0 μL, Split, Split Ratio 8.0:1 |
| Injector Port Temperature | 250° C. |
| **Oven Conditions** | |
| Initial Temperature | 40° C. |
| Hold Time | 2 minutes |
| Ramp | 5° C./min |
| Final Temperature | 270° C. |
| Final Hold | 6 minutes |
| Total Run Time | 54.0 minutes |
| **Mass Spectrophotometer Detector Conditions** | |
| MS Source Temperature | 230° C. |
| MS Quad | 150° C. |
| Back Detector | 270° C. |

TABLE 3-continued

| GC CONDITIONS | |
|---|---|
| Tune File | Atune.u |
| Scan Range | 40 to 600 amu |
| Solvent Delay | 4.5 minutes |

Calculate the average Response Factor of total area sum from standard calibration curve. See equation below:

$$RF=((Ax)*(Cis)/((Ais)(Cx))$$

where:

AX=Area of the compound

CX=Standard Concentration (mg)

Ais=Area of the internal standard

Cis=Internal Standard Concentration (mg)

Calculate sample concentration (mg). See equation below:

$$CXs=(((Ax)*(Cis)/((Ais)(RFAVE)))*df$$

where:

AX=Area of the compound

CXs=Sample Concentration (mg)

Ais=Area of the internal standard

RFAVE=Average Response Factor df=Sample Dilution

By using the sample concentration (mg) of perfume oil found in the isooctane extract and dividing by the theoretical perfume dosed into the fabric softener, one can calculate the amount of perfume that has leaked out of the microcapsule during aging.

Biodegradability Test Method

Biodegradability testing is carried out according to protocol OECD 301D. The microcapsule membrane is isolated by going through the following steps: (1) Lyophilize the microcapsule slurry sample (for spray dry powder version of microcapsules lyophilization is not needed), (2) Methanol/toluene extraction of the lyophilized solids or spray dry powder capsules to assure less than 5% residual oil or active materials, (3) filtration of the solvent and extracted material, (4) vacuum drying at room temperature to 60° C. and 0.3 torr for 24 hours, (5) water extraction of the dried powder to remove any water soluble components in the membrane, followed by filtration to recover the membrane part of capsule particles, (6) vacuum dry the powder to remove residual water at 0.3 torr for 1 day at room temperature to 60° C. The isolated membrane polymer of capsule is then subjected to OECD 301D protocol, available at https://www.oecd.org/chemicalsafety/risk-assessment/1948209.pdf, with the following experimental conditions:

1) test substance concentration in the mineral medium is 5 mg/L.
2) 300 mL Biological Oxygen Demand (BOD) bottles with glass stoppers are used.
3) An incubator at 20° C. is used to age the samples in the dark.
4) The mineral stock solutions as provided in the method are prepared.
5) After letting the secondary effluent settle for at least 1 hour, a 10× (10 mL of secondary effluent is added to 90 mL of deionized water) secondary effluent is prepared with BOD water to make 100 mL total inoculum in a beaker. Then 0.5 mL of the 10× inoculum is added to each BOD bottle.
6) COD of the isolated polymer is measured using Hach kit.

The bottles are checked for dissolved oxygen at 0 days, 7, 14, 28, and 60 days. The percent degradation is analyzed via the calculations taught in the OECD 301D method.

Example 1—Amine and Acid Functional Urea Linked Amino Acid Isocyanate Adducts

Example 1A

Weigh out 570 g water into a reaction kettle. Add 326 g lysine hydrochloride under agitation at room temperature. To this solution, add 178.48 g 40% sodium hydroxide aqueous solution under agitation. Continue agitation until temperature comes down to nearly 25° C. Add 198.12 g isophorone diisocyanate under agitation at room temperature. Raise temperature to 35-40° C. and continue reaction for 2 hours. Set temperature to 60° C. and continue reaction for 2 hours. Cool down to 35° C. under agitation and add 178.48 g 40% sodium hydroxide solution. The product, amine terminated diamino-diurea-disodium carboxylate of 34.40% in water, is synthesized by this technique and abbreviated here as X1.

Example 1B

Weigh out 520 g water into a reaction kettle. Add 100 g lysine hydrochloride under agitation at room temperature. To this solution, add 54.74 g 40% sodium hydroxide aqueous solution under agitation. Continue agitation until temperature comes down to nearly 25° C. Add 47.69 g toluene diisocyanate dropwise under agitation. Addition of toluene diisocyanate raised temperature to 35-40° C. Continue reaction for 2 hours at 40° C. Set temperature to 60° C. and continue reaction for 2 hours. Cool down to 50° C. under agitation and add 54.74 g 40% sodium hydroxide solution. The product, amine terminated diamino-diurea-disodium carboxylate of 18.06% in water, is synthesized by this technique and abbreviated here as X2. A common and representative scheme of amine-acid functional urea linked amino acid isocyanate adduct synthesis is depicted in FIG. 1.

Example 2—Amine-Hydroxy-Acid Functional Amino Acid Epoxide Adduct

Figure 2:
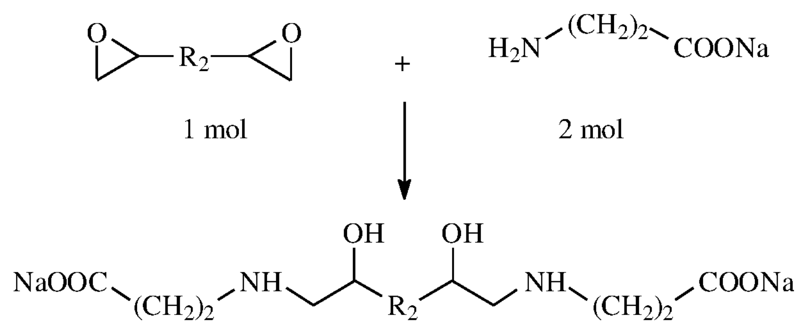
FIG. 2 is a non-limiting example of a synthetic scheme for the preparation of an embodiment of an amino acid epoxide adduct in accordance with the second aspect of the invention.

Weigh out 1032 g water into a reaction kettle. Add 200 g beta alanine under agitation at room temperature. To this solution, add 224.46 g 40% sodium hydroxide aqueous solution under agitation. Raise the temperature of this solution to 75° C. Add 272.72 g resorcinol diglycidyl ether dropwise under agitation below the temperature 85° C. Addition of this diepoxy may raise the temperature to 85° C. Continue reaction for 1 hours at 85° C. Cool down to room temperature under agitation. The product, secondary amine functional diamino-diol-disodium carboxylate of 30.19% in water, is synthesized by this technique and abbreviated here as X3. A common and representative scheme of amine-hydroxy-acid functional amino acid epoxide adduct synthesis is depicted in FIG. 2.

Example 3—Treated Protein Isolate

Example 3A

This special treatment of protein isolate enhances solubility or dispersibility as well as reactive moieties of protein isolate. Weigh out 600 g distilled water into a reaction kettle. Raise temperature to 65° C. under agitation. Add 80 g pea protein isolate powder into the kettle while temperature is rising. Once the temperature is steady at 65° C., add 6.25 g 40% sodium hydroxide and agitate for 1 hour. Cool down to 50° C. and adjust pH to 7.5 by adding 7.25 g 20% hydrochloride solution. The specially treated protein isolate by this technique and composition is abbreviated here as PS1.

Example 3B

Weigh out 650 g distilled water into a reaction kettle. Raise temperature to 65° C. under agitation. Add 90 g pea protein isolate powder into the kettle while temperature is rising. Once the temperature is steady at 65° C., add 5.25 g 40% sodium hydroxide and agitate for 1 hour. Cool down to 50° C. and adjust pH to 7.5 by adding 6.25 g 20% hydrochloride solution. The specially treated protein isolate by this technique and composition is abbreviated here as PS2.

Example 3C

Weigh out 675 g distilled water into a reaction kettle. Raise temperature to 65° C. under agitation. Add 95 g pea protein isolate powder into the kettle while temperature is rising. Once the temperature is steady at 65° C., add 5.25 g 40% sodium hydroxide and agitate for 1 hour. Cool down to 50° C. and adjust pH to 7.5 by adding 6.25 g 20% hydrochloride solution. The specially treated protein isolate by this technique and composition is abbreviated here as PS3.

Example 3D

Weigh out 675 g distilled water into a reaction kettle. Raise temperature to 65° C. under agitation. Add 95 g pea protein isolate powder into the kettle while temperature is rising. Once the temperature is steady at 65° C., add 5.25 g 40% sodium hydroxide and agitate for 30 minutes. Cool down to 50° C. and adjust pH to 7.5 by adding 6.25 g 20% hydrochloride solution. The specially treated protein isolate by this technique and composition is abbreviated here as PS4.

Example 3E

Weigh out 750 g distilled water into a reaction kettle. Raise temperature to 65° C. under agitation. Add 95 g mung protein isolate powder into the kettle while temperature is rising. Once the temperature is steady at 65° C., add 2.75 g 40% sodium hydroxide and agitate for 1 hour. Cool down to 50° C. and adjust pH to 7.5 by adding 3.25 g 20% hydrochloride solution. The specially treated protein isolate by this technique and composition is abbreviated here as PS5.

Example 3F

Weigh out 750 g distilled water into a reaction kettle. Raise temperature to 65° C. under agitation. Add 95 g mung protein isolate powder into the kettle while temperature is rising. Once the temperature is steady at 65° C., add 2.75 g 40% sodium hydroxide and agitate for 30 minutes. Cool down to 50° C. and adjust pH to 7.5 by adding 3.25 g 20% hydrochloride solution. The specially treated protein isolate by this technique and composition is abbreviated here as PS6.

Example 4 Environmentally Biodegradable Controlled Release Particles

Example 4A

Weigh out 693.51 g specially treated protein isolate PS1 into a reaction kettle. Add 180 g 5% gelatinized starch dispersion into the kettle under agitation. Then, add 0.90 g 70% nonylphenyl ethoxylated surfactant (of HLB~17.8) and heat liquid in the kettle to 35° C. under agitation. In the meantime, prepare active perfume phase in 300 mL jar. Weigh out 130 g perfume, 10 g diphenyldiisocyanate based polymeric isocyanate, 11 g trimethylolpropane-xylene-diisocyanate adduct based triisocyanate, 2 g tetraglycidyl ether sorbitol, 1.5 g epoxy phenol novolac triglycidyl ether, 1.5 g 3-glycidyloxypropyl trimethoxy silane, 1.5 g ester-based polymeric plasticizer into a 300 mL jar and agitate for 30 minutes. Add this perfume phase into the aqueous phase (in the kettle) under the agitation of 900 rpm at 35° C. After 15 minutes, adjust pH to 7.5 by adding 5.29 g 20% sodium carbonate aqueous solution. Set temperature to 40° C. of kettle while agitating. Then after 15 minutes, raise pH to 8.5 by adding 3.57 g 20% sodium metasilicate aqueous solution. Allow reaction for 45 minutes at 40° C. under agitation and then set to raise temperature to 60° C. Once the temperature is steady at 60° C., add combined solution of 6 g X1 and 6 g X3 crosslinkers dropwise into the reaction kettle. Allow reaction to happen at 60° C. under agitation for 5 hours. Cool down to room temperature and adjust pH to 7.5 by adding 4.05 g 20% hydrochloride aqueous solution. Add 165 g distilled water and agitate for 10 minutes and then spray dry slurry to obtain powder version of perfume encapsulated microcapsule. This dry powder version of microcapsules contains 51.85% perfume.

Example 4B

Weigh out 693.51 g specially treated protein isolate PS1 into a reaction kettle. Add 180 g 5% gelatinized starch solution into the kettle under agitation. Then, add 0.90 g 70% nonylphenyl ethoxylated surfactant (of HLB~17.8) and heat liquid in the kettle to 35° C. under agitation. In the meantime, prepare active perfume phase in 300 mL jar. Weigh out 130 g perfume, 10 g diphenyldiisocyanate based polymeric isocyanate, 11 g trimethylolpropane-xylenediisocyanate adduct based triisocyanate, 2 g tetraglycidyl ether sorbitol, 1.5 g epoxy phenol novolac triglycidyl ether, 1.5 g 3-glycidyloxypropyl trimethoxy silane, 1.5 g ester-based polymeric plasticizer into 300 mL jar and agitate for 30 minutes. Add this perfume phase into the aqueous phase (in the kettle) under the agitation of 900 rpm at 35° C. After 15 minutes, adjust pH to 7.5 by adding 5.29 g 20% sodium carbonate aqueous solution. Set temperature to 40° C. in the kettle while agitating. Then after 15 minutes, raise pH to 8.5 by adding 3.57 g 20% sodium metasilicate aqueous solution. Allow reaction for 45 minutes at 40° C. under agitation and then set to raise temperature to 60° C. Once the temperature is steady at 60° C., add combined solution of 6 g X1 and 6 g X3 crosslinkers dropwise into the reaction kettle. Allow reaction to happen at 60° C. under agitation for 5 hours. Cool down to room temperature and adjust pH to 6.75 by adding 5.25 g 20% hydrochloride aqueous solution. Add 5 g chitosan powder and agitate for 30 minutes at room temperature. Add 165 g distilled water and agitate for 10 minutes and then spray dry slurry to obtain powder version of perfume encapsulated microcapsule. This dry powder version of microcapsules contains 50.81% perfume.

Example 4C

Weigh out 693.51 g specially treated protein isolate PS1 into a reaction kettle. Then, add 0.90 g 70% nonylphenyl ethoxylated surfactant (of HLB~17.8) under agitation and heat liquid in the kettle to 35° C. under agitation. In the meantime, prepare active perfume phase in a 300 mL jar. Weigh out 130 g perfume, 7.5 g diphenyldiisocyanate based polymeric isocyanate, 15 g trimethylolpropane-xylenediisocyanate adduct based triisocyanate, 2.25 g tetraglycidyl ether sorbitol, 2.25 g epoxy phenol novolac triglycidyl ether, 2.25 g 3-glycidyloxypropyl trimethoxy silane, 2.0 g sorbitol powder, 1.5 g ester based polymeric plasticizer into 300 mL jar and agitate for 30 minutes. Then add 2.0 g finely powdered sorbitol into active perfume phase and mix at 10000 rpm at room temperature for 1 minute. Add this perfume phase into the aqueous phase (in the kettle) under the agitation of 700 rpm at 35° C. After 15 minutes, adjust pH to 7.5 by adding 7.95 g 20% sodium carbonate aqueous solution. Set temperature to 40° C. of kettle while agitating. Then after 15 minutes, raise pH to 8.25 by adding 11.05 g 20% sodium metasilicate aqueous solution. Allow reaction for 45 minutes at 40° C. under agitation and then set to raise temperature to 60° C. Once the temperature is steady at 60° C., add combined solution of 3.5 g X1 and 3.5 g X2 crosslinkers dropwise into the reaction kettle. Allow reaction to happen at 60° C. under agitation for 5 hours. Cool down to room temperature and adjust pH to 6.0 by adding 12.75 g 20% hydrochloride aqueous solution. In the meantime, prepare aqueous solution of tetrahydroxy orthosiloxane or orthosilicic acid by acidic hydrolysis of tetraethylorthosiloxane (TEOS) in water followed by removal of ethanol. Weigh out 65 g tetraethyl orthosilicate and 65 g of distilled water into a separate and small reaction kettle and add few drops of 20% hydrochloride aqueous solution to adjust pH to ~2 and agitate at 45° C. for nearly about 30 minutes. Rota-vap this freshly produced orthosilicic acid at 35° C. to remove ethanol. Add 25 g of 31.58% aqueous solution of orthosilicic acid and agitate for 4 hours at room temperature. Add 200 g water and add 3.0 g chitosan powder and agitate for 30 minutes at room temperature. Add 50 g 5% gelatinized starch aqueous solution and agitate for 30 minutes and then spray dry slurry to obtain powder version of perfume encapsulated microcapsule. This dry powder version of microcapsules contains 50.34% perfume.

Example 4D

Weigh out 751.5 g specially treated protein isolate PS2 into a reaction kettle. Then, add 0.90 g 70% nonylphenyl ethoxylated surfactant (of HLB~17.8) and heat liquid in the kettle to 35° C. under agitation. In the meantime, prepare active perfume phase in 300 mL jar. Weigh out 135 g perfume, 5.63 g diphenyldiisocyanate based polymeric isocyanate, 11.25 g trimethylolpropane-xylenediisocyanate adduct based triisocyanate, 1.69 g tetraglycidyl ether sorbitol, 1.69 g epoxy phenol novolac triglycidyl ether, 1.69 g 3-glycidyloxypropyl trimethoxy silane, 1.7 g ester based polymeric plasticizer into 300 mL jar and agitate for 30 minutes. Add 2.0 g finely powdered sorbitol into active perfume phase and agitate at 10000 rpm at room temperature for 1 minute. Add this perfume phase into the aqueous phase (in the kettle) under the agitation of 750 rpm at 35° C. After 15 minutes, adjust pH to 7.5 by adding 4.25 g 20% sodium carbonate aqueous solution. Set temperature to 40° C. in the kettle while agitating. Then after 15 minutes, raise pH to 8.25 by adding 5.56 g 20% sodium metasilicate aqueous solution. Allow reaction for 45 minutes at 40° C. under agitation and then set to raise temperature to 60° C. Once the temperature is steady at 60° C., add combined solution of 3.15 g X1 and 3.15 g X3 crosslinkers dropwise into the reaction kettle. Allow reaction to happen at 60° C. under agitation for 5 hours. Cool down to room temperature and adjust pH to 6.0 by adding 4.5 g 20% hydrochloride aqueous solution. Add 20.91 g of 31.58% aqueous solution of orthosilicic acid (freshly prepared as per mention in example 4C) and agitate for 4 hours at room temperature. Add 160 g water and add 3.94 g chitosan powder and agitate for 30 minutes at room temperature. Add 56.25 g 5% gelatinized starch aqueous solution and agitate for 30 minutes and then spray dry slurry to obtain powder version of perfume encapsulated microcapsule. This dry powder version of microcapsules contains 51.18% perfume.

Example 4E

Weigh out 781.5 g specially treated protein isolate PS3 into a reaction kettle and add 170 g water. Then, add 0.90 g 70% nonylphenyl ethoxylated surfactant (of HLB~17.8) and heat liquid in the kettle to 35° C. under agitation. In the meantime, prepare active perfume phase in 300 mL jar. Weigh out 135 g perfume, 5.63 g diphenyldiisocyanate based polymeric isocyanate, 11.25 g trimethylolpropane-xylenediisocyanate adduct based triisocyanate, 1.69 g tetraglycidyl ether sorbitol, 1.69 g epoxy phenol novolac triglycidyl ether, 1.69 g 3-glycidyloxypropyl trimethoxy silane, 1.7 g polyadipate ester into 300 mL jar and agitate for 30 minutes. Add 2.0 finely powdered sorbitol into active perfume phase and agitate at 10000 rpm at room temperature for 1 minute. Add this perfume phase into the aqueous phase (in the kettle) under the agitation of 750 rpm at 35° C. After 15 minutes, adjust pH to 7.5 by adding 4.5 g 20% sodium carbonate aqueous solution. Set temperature to 40° C. in the kettle while agitating. Then after 15 minutes, raise pH to 8.25 by adding 5.58 g 20% sodium metasilicate aqueous solution. Allow reaction for 45 minutes at 40° C. under agitation and then set to raise temperature to 60° C. Once the temperature is steady at 60° C., add combined solution of 3.15 g X1 and 3.15 g X3 crosslinkers dropwise into the reaction kettle. Allow reaction to happen at 60° C. under agitation for 5 hours. Cool down to room temperature and adjust pH to 6.0 by adding 4.6 g 20% hydrochloride aqueous solution. Add 20.91 g of 31.58% aqueous solution of orthosilicic acid (freshly prepared as per mention in example 4C) and agitate for 4 hours at room temperature. Add 200 g water and add 3.94 g chitosan powder and agitate for 30 minutes at room temperature. Add 56 g 5% gelatinized starch aqueous solution and agitate for 30 minutes and then spray dry slurry to obtain powder version of perfume encapsulated microcapsule. This dry powder version of microcapsules contains 50.25% perfume.

Example 4F

Weigh out 781.5 g specially treated protein isolate PS4 into a reaction kettle and add 170 g water. Then, add 0.90 g 70% nonylphenyl ethoxylated surfactant (of HLB~17.8) and heat liquid in the kettle to 35° C. under agitation. In the meantime, prepare active perfume phase in 300 mL jar. Weigh out 135 g perfume, 5.63 g diphenyldiisocyanate based polymeric isocyanate, 11.25 g trimethylolpropane-xylenediisocyanate adduct based triisocyanate, 1.69 g tetraglycidyl ether sorbitol, 1.69 g epoxy phenol novolac triglycidyl ether, 1.69 g 3-glycidyloxypropyl trimethoxy silane, 1.7 g polyadipate ester into 300 mL jar and agitate for 30 minutes. Add 2.0 finely powdered sorbitol into active perfume phase and agitate at 10000 rpm at room temperature for 1 minute. Add this perfume phase into the aqueous phase (in the kettle) under the agitation of 750 rpm at 35° C. After 15 minutes, adjust pH to 7.5 by adding 4.5 g 20% sodium carbonate aqueous solution. Set temperature to 40° C. in the kettle while agitating. Then after 15 minutes, raise pH to 8.25 by adding 5.58 g 20% sodium metasilicate aqueous solution. Allow reaction for 45 minutes at 40° C. under and then set to raise temperature to 60° C. Once the temperature is steady at 60° C., add combined solution of 3.15 g X1 and 3.15 g X3 crosslinkers dropwise into the reaction kettle. Allow reaction to happen at 60° C. under agitation for 5 hours. Cool down to room temperature and adjust pH to 6.0 by adding 4.6 g 20% hydrochloride aqueous solution. Add 20.91 g of 31.58% aqueous solution of orthosilicic acid (freshly prepared as per mention in example 4C) and agitate for 4 hours at room temperature. Add 200 g water and add 3.94 g chitosan powder and agitate for 30 minutes at room temperature. Add 56 g 5% gelatinized starch aqueous solution and agitate for 30 minutes and then spray dry slurry to obtain powder version of perfume encapsulated microcapsule. This dry powder version of microcapsules contains 50.126% perfume.

Example 4G

Weigh out 851 g specially treated protein isolate PS5 into a reaction kettle and add 170 g water. Then, add 0.90 g 70% nonylphenyl ethoxylated surfactant (of HLB~17.8) and heat liquid in the kettle to 35° C. under agitation. In the meantime, prepare active perfume phase in 300 mL jar. Weigh out 135 g perfume, 5.63 g diphenyldiisocyanate based polymeric isocyanate, 11.25 g trimethylolpropane-xylenediisocyanate adduct based triisocyanate, 1.69 g tetraglycidyl ether sorbitol, 1.69 g epoxy phenol novolac triglycidyl ether, 1.69 g 3-glycidyloxypropyl trimethoxy silane, 1.7 g polyadipate ester into 300 mL jar and agitate for 30 minutes. Add 2.0 finely powdered sorbitol into active perfume phase and agitate at 10000 rpm at room temperature for 1 minute. Add this perfume phase into the aqueous phase (in the kettle) under the agitation of 750 rpm at 35° C. After 15 minutes, adjust pH to 7.5 by adding 4.5 g 20% sodium carbonate aqueous solution. Set temperature to 40° C. in the kettle while agitating. Then after 15 minutes, raise pH to 8.25 by adding 5.58 g 20% sodium metasilicate aqueous solution. Allow reaction for 45 minutes at 40° C. under agitation and then set to raise temperature to 60° C. Once the temperature is steady at 60° C., add combined solution of 3.15 g X1 and 3.15 g X3 crosslinkers dropwise into the reaction kettle. Allow reaction to happen at 60° C. under agitation for 5 hours. Cool down to room temperature and adjust pH to 6.0 by adding 4.6 g 20% hydrochloride aqueous solution. Add 20.91 g of 31.58% aqueous solution of orthosilicic acid (freshly prepared as per mention in example 4C) and agitate for 4 hours at room temperature. Add 200 g water and add 3.94 g chitosan powder and agitate for 30 minutes at room temperature. Add 56 g 5% gelatinized starch aqueous solution and agitate for 30 minutes and then spray dry slurry to obtain powder version of perfume encapsulated microcapsule. This dry powder version of microcapsules contains 50.04% perfume.

Example 4H

Weigh out 851 g specially treated protein isolate PS6 into a reaction kettle and add 170 g water. Then, add 0.90 g 70% nonylphenyl ethoxylated surfactant (of HLB~17.8) and heat liquid in the kettle to 35° C. under agitation. In the meantime, prepare active perfume phase in 300 mL jar. Weigh out 135 g perfume, 5.63 g diphenyldiisocyanate based polymeric isocyanate, 11.25 g trimethylolpropane-xylenediisocyanate adduct based triisocyanate, 1.69 g tetraglycidyl ether sorbitol, 1.69 g epoxy phenol novolac triglycidyl ether, 1.69 g 3-glycidyloxypropyl trimethoxy silane, 1.7 g polyadipate ester into 300 mL jar and agitate for 30 minutes. Add 2.0 finely powdered sorbitol into active perfume phase and agitate at 10000 rpm at room temperature for 1 minute. Add this perfume phase into the aqueous phase (in the kettle) under the agitation of 750 rpm at 35° C. After 15 minutes, adjust pH to 7.5 by adding 4.5 g 20% sodium carbonate aqueous solution. Set temperature to 40° C. in the kettle while agitating. Then after 15 minutes, raise pH to 8.25 by adding 5.58 g 20% sodium metasilicate aqueous solution. Allow reaction for 45 minutes at 40° C. under agitation and then set to raise temperature to 60° C. Once the temperature is steady at 60° C., add combined solution of 3.15 g X1 and 3.15 g X3 crosslinkers dropwise into the reaction kettle. Allow reaction to happen at 60° C. under agitation for 5 hours. Cool down to room temperature and adjust pH to 6.0 by adding 4.6 g 20% hydrochloride aqueous solution. Add 20.91 g of 31.58% aqueous solution of orthosilicic acid (freshly prepared as per mention in example 4C) and agitate for 4 hours at room temperature. Add 200 g water and add 3.94 g chitosan powder and agitate for 30 minutes at room temperature. Add 56 g 5% gelatinized starch aqueous solution and agitate for 30 minutes and then spray dry slurry to obtain powder version of perfume encapsulated microcapsule. This dry powder version of microcapsules contains 50.06% perfume.

Figure 3:
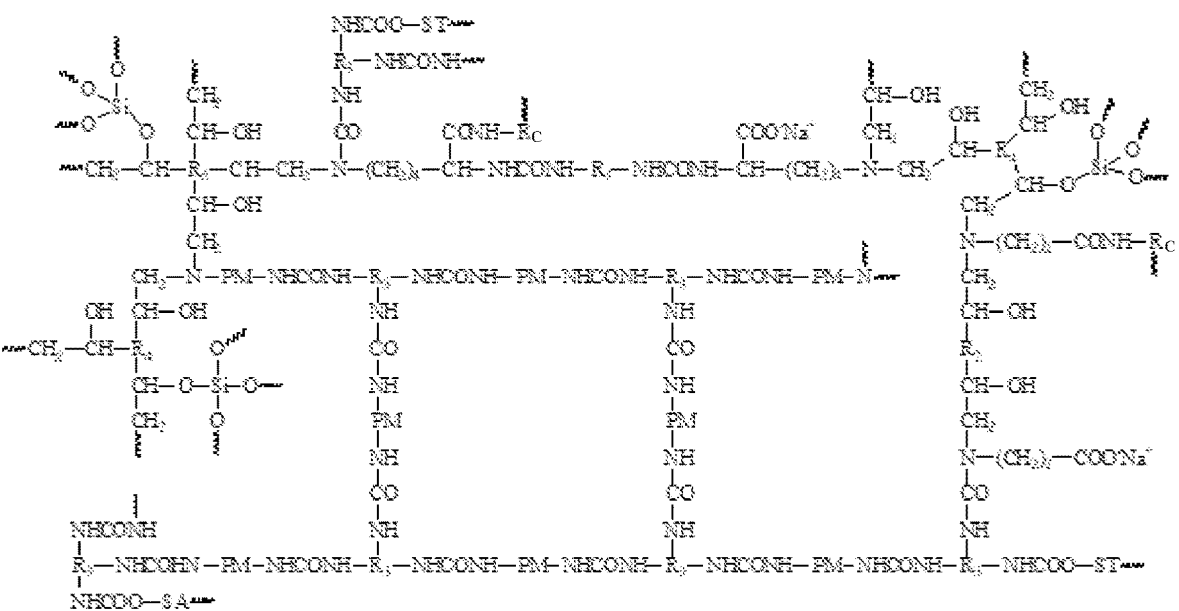
FIG. 3 shows the chemical structure of a crosslinked polymer of a microcapsule shell prepared according to Examples 4A-4H.

FIG. 3 shows the chemical structure of a crosslinked polymer of a microcapsule shell prepared according to Examples 4A-4H, where $R_3$ is a moiety of a monomer or prepolymer having three reactive —NCO functional groups; $R_4$ is a moiety of a monomer or prepolymer having three reactive glycidyl ether epoxide groups; $R_5$ is a moiety of a monomer or prepolymer having four reactive glycidyl ether epoxide groups; $R_C$ is chitosan moiety; ST is a starch moiety; PM is an amide-linked polypeptide or protein moiety; and SA is a sugar alcohol moiety.

Example 4I

Weigh out 436.45 g specially treated protein isolate PS2 into a reaction kettle. Then, add 0.5 g secondary alcohol ethoxylated surfactant (of HLB~18) and heat liquid in the kettle to 35° C. under agitation. In the meantime, prepare active perfume phase in 300 mL jar. Weigh out 162.5 g perfume, 2.0 g diphenyldiisocyanate based polymeric isocyanate, 4.0 g trimethylolpropane-xylenediisocyanate adduct based triisocyanate, 0.57 g tetraglycidyl ether sorbitol, 0.57 g epoxy phenol novolac triglycidyl ether, 0.57 g 3-glycidyloxypropyl trimethoxy silane, 2.0 g ester based polymeric plasticizer into 300 mL jar and agitate for 30 minutes. Add 2.0 g finely powdered sorbitol into active perfume phase and agitate at 10000 rpm at room temperature for 1 minute. Add this perfume phase into the aqueous phase (in the kettle) under the agitation of 725 rpm at 35° C. After 10 minutes, adjust pH to 7.5 by adding 1.5 g 20% sodium carbonate aqueous solution. Set temperature to 40° C. in the kettle while agitating. Then after 10 minutes, raise pH to 8.5 by adding 2.25 g 20% sodium metasilicate aqueous solution. Allow reaction for 45 minutes at 40° C. under agitation and then set to raise temperature to 60° C. Once the temperature is steady at 60° C., add combined solution of 14.91 g X1 and 14.91 g X3 crosslinkers dropwise into the reaction kettle. Allow reaction to happen at 60° C. under agitation for 4 hours. Cool down to 55° C. temperature and add 100 g 25% octenyl succinic anhydride modified starch solution. Agitate 30 minutes while cooling down to 35° C. Add 53.50 g 10% sodium metasilicate maintaining pH between 7.75-8.75 by adding 10% HCl solution. Leave final pH at 8.05. Add 140.50 g 5% gelatinized starch solution and continue agitation for 30 minutes. Add 150 g water under agitation. Spray dry slurry to obtain powder version of perfume encapsulated microcapsule. This dry powder version of microcapsules contains 58.83% perfume.

Example 5—Performance Testing

Microcapsules slurries are formulated into liquid fabric softener (DOWNY FREE), to deliver approximately 0.40 wt. % fragrance usage level in the liquid suspension, via the microcapsules or neat perfume oil. These samples are used for leakage stability testing and performance testing. The prepared mixtures are aged for 1 week at 40° C. After ageing, approximately 30 g of the aged liquid fabric softener is added to a Samsung front load washing machine fabric softener compartment. Approximately 4 bath towels and 4 polycotton T-shirts are added to the washing machine. A quick cycle (25 minute cold wash cycle that has 2 rinse cycles) is completed. The washed fabrics are dried using the high heat setting in a Samsung dryer. Fabrics are aged for 24 hours, and then evaluated for pre-rub and post-rub fabric odor.

Microcapsules slurries are formulated into liquid detergent (TIDE FREE & CLEAR) to deliver approximately 0.40 wt. % fragrance usage level in the liquid suspension, via the microcapsules or neat perfume oil. These samples are used for leakage stability testing and performance testing. The prepared mixtures are aged for 1 week at 40° C. After ageing, approximately 30 g of the aged liquid detergent is added to a Samsung front load washing machine detergent compartment. Approximately 4 bath towels and 4 polycotton T-shirts are added to the washing machine. A quick cycle (25 minute cold wash cycle that has 2 rinse cycles) is completed. The washed fabrics are dried using the high heat setting in a Samsung dryer. Fabrics are aged for 24 hours, and then evaluated for pre-rub and post-rub fabric odor.

TABLE 5-1

Laundered fabric odor performance of spray dried microcapsules aged in liquid fabric softener for 1 week at 40° C.

| ID | Description of Capsule | Odor Grade Pre-Rub/Post-Rub | Leakage 1 wk/40° C. |
|---|---|---|---|
| Example 5A | Example 4C Capsules | 1.5/4 | 10% |

TABLE 5-2

Laundered fabric odor performance of spray dried microcapsules aged in liquid detergent for 1 week at 40° C.

| ID | Description of Capsule | Odor Grade Pre-Rub/Post-Rub | Leakage 1 wk/40° C. |
|---|---|---|---|
| Example 5B | Example 4C Capsules | 1/4 | 12% |

TABLE 5-3

Performance Grading Scale for laundered fabrics

| Pre-Rub or Post-Rub Odor Grade | Description |
|---|---|
| 0 | No odor |
| 1 | Slight odor |
| 2 | Noticeable odor |
| 3 | Highly Noticeable, obvious odor |
| 4 | Strong and highly impactful odor |

Spray dried microcapsules of Example 4A are added to the detergent sheets disclosed in US 202110261885A1, Example 1, Final Solution process given in at paragraph 109 and composition given in paragraph 116, to deliver 0.075 grams of fragrance oil into the washing machine. The sheet and microcapsules are added to a Samsung front load washing machine detergent compartment. Approximately 4 bath towels and 4 polycotton T-shirts are added to the washing machine. A quick cycle (25 minute cold wash cycle that has 2 rinse cycles) is completed. The washed fabrics are dried using the high heat setting in a Samsung dryer. Fabrics are aged for 24 hours, and then evaluated for pre-rub and post-rub fabric odor.

TABLE 5-4

Laundered fabric odor performance of spray dried microcapsules in water soluble detergent substrate.

| ID | Description of Capsule | Odor Grade Pre-Rub/Post-Rub |
|---|---|---|
| Example 5C | Example 4A Capsules | 1/4 |

TABLE 5-5

Performance Grading Scale for laundered fabrics

| Pre-Rub or Post-Rub Odor Grade | Description |
|---|---|
| 0 | No odor |
| 1 | Slight odor |
| 2 | Noticeable odor |
| 3 | Highly Noticeable, obvious odor |
| 4 | Strong and highly impactful odor |

The data clearly indicate a bloom of fragrance oil from fabrics upon rubbing, indicating a sufficient retention of capsules on fabric, and the fracture of such capsules to release the encapsulated fragrance oil.

Example 5B Environmental Biodegradability

Microcapsules of various examples above were evaluated for environmental biodegradability by adapting the OCDE/OECD 301D Closed Bottle Test method, as described in the Biodegradability test method description.

The spray dried microcapsules of Example 3 were first extracted with methanol/toluene to remove the encapsulated perfume oil (12:1 ratio), and filtered. After vacuum drying, the powder was extracted with water (50:1 ratio) and filtered. The powder was vacuum dried, ground into a fine powder using a mortar/pestle, and these isolated polymers were subjected to biodegradability testing.

TABLE 5B-1

| Mineral Oil Solutions | | | |
|---|---|---|---|
| Mineral Solution ID | Ingredient | Formula | Mass (g) |
| A | Potassium dihydrogen orthophosphate | $KH_2PO_4$ | 8.50 |
| | Dipostassium hydrogen orthophosphate | $K_2HPO_4$ | 21.75 |
| | Disodium hydrogen orthophosphate dehydrate | $Na_2HPO_4$—$2H_2O$ | 33.40 |
| | Ammonium chloride | $NH_4Cl$ | 0.50 |
| | Dissolve in water and bring to 1 L. pH to 7.4 | | |
| B | Calcium Chloride anhydrous | $CaCl_2$ | 27.50 |
| | OR | | |
| | Calcium Chloride dehydrate | $CaCl_2$—$2H_2O$ | 36.40 |
| | Dissolve in water and bring to 1 L. | | |
| C | Magnesium sulfate heptahydrate | $MgSO_4$—$7H_2O$ | 22.50 |
| | Dissolve in water and bring to 1 L. | | |
| D | Iron (III) chloride hexahydrate | $FeCl_3$—$6H_2O$ | 0.25 |
| | Dissolve in water and bring to 1 L. | | |

Prepare approximately 300 mL solutions containing the particles to be tested (approximately 1.5 milligrams of the isolated polymer is added to each BOD bottle). Fill BOD bottles (300 mL capacity) just past the neck of the bottle. Insert stopper. Store BOD bottles in the dark in an incubator maintained at 20° C. Use dissolved oxygen meter (YSI 5000), and YSI5905 Dissolved Oxygen meter probe to measure oxygen at specific time points.

The dissolved oxygen measured values as a function of time, and the calculation methods presented in OECD 301D method are utilized to calculate the % biodegradability. The Environmental Biodegradability index is calculated by multiplying the measured % biodegradability by 100. The results are listed in Table 5B-2 below.

TABLE 5B-2

| Environmental Biodegradability Results of isolated polymers of the following example controlled release particles | | |
|---|---|---|
| Membrane from Microcapsule of Example: | OECD 301D % Biodegradability (60 day) | Biodegradability Index |
| Example 4A TCJD120123-DZ-5 | 72% | 72 |
| Example 4B TCJD111523-DY-7 | 55% | 55 |
| Example 4C TCJD120123-DZ-7 | 66% | 66 |
| Example 4D TCJD122723-EA-1 | 67% | 67 |

A biodegradability index greater than 60 meets current ECHA requirements for microplastics biodegradability (2019).

Example 6—Hair Conditioner

Selected microcapsules from the above examples are formulated into a leave-on-conditioner formulation as follows: to 98.0 grams of leave-on-conditioner (with a typical formulation given below) is added an appropriate amount of microcapsule slurry or spray dried microcapsules of Example 4, to deliver an encapsulated oil usage level of 0.5 wt. %. The microcapsules are added on top of the conditioner formulation, then the contents are mixed at 1000 RPM for 1 minute.

A typical composition of a leave-on conditioner formulation is given in Table 6.1 below.

TABLE 6.1

| Hair Condition Formulation | |
|---|---|
| Components | Ex. I (LOT) (%) |
| Premix | |
| Aminosilicone | — |
| PDMS | 1.0-1.5 |
| Gel matrix carrier | |
| Behenyl trimethyl ammonium chloride | — |
| Stearamidopropyldimethylamine (SAPDMA), C18 | 0.60-0.8 |
| DTDMAC, C18(Quaternium-18) | 0.45-0.6 |
| Citric Acid (anhydrous) | 0.10-0.25 |
| Cetyl alcohol | 0.80-1.0 |
| Stearyl alcohol | 0.54-1.0 |
| Deionized Water | Balance |
| Polymers | |
| Hydroxyethylcellulose (HEC) | 0.15-0.50 |
| PEG-2M (Polyox WAR N-10) | 0.30-0.60 |
| Others | |
| Preservatives | 0.40-0.60 |

Example 7—Shampoo

Selected microcapsules from the above examples are formulated into a rinse-off shampoo formulation as follows: to 90.0 grams of shampoo formulation is added an appropriate amount of microcapsule slurry or spray dried microcapsules of Examples 4, to deliver an encapsulated oil usage level of 0.5 wt. %. The microcapsules and water are added on top of the shampoo formulation, then the contents are mixed at 1850 RPM for 1 minute. Typical shampoo formulations are shown in Tables 7.1, 7.2 and 7.3 below.

TABLE 7.1

| Shampoo Formulations of Examples 7A-7C. | | | |
|---|---|---|---|
| | Example | | |
| Ingredient | 7A | 7B | 7C |
| Water | q.s. | q.s. | q.s. |
| Polyquaternium 76 [1] | 2.50 | — | — |
| Guar, Hydroxylpropyl Trimonium Chloride [2] | — | 0.25 | — |
| Polyquaterium 6 [3] | — | — | 0.79 |
| Sodium Laureth Sulfate (SLE3S) [4] | 21.43 | 21.43 | 21.43 |
| Sodium Lauryl Sulfate (SLS) [5] | 20.69 | 20.69 | 20.69 |
| Silicone [6] | 0.75 | 1.00 | 0.5 |
| Cocoamidopropyl Betaine [7] | 3.33 | 3.33 | 3.33 |
| Cocoamide MEA [8] | 1.0 | 1.0 | 1.0 |
| Ethylene Glycol Distearate [9] | 1.50 | 1.50 | 1.50 |
| Sodium Chloride [10] | 0.25 | 0.25 | 0.25 |

TABLE 7.1-continued

Shampoo Formulations of Examples 7A-7C.

| Ingredient | Example 7A | 7B | 7C |
|---|---|---|---|
| Fragrance | 0.70 | 0.70 | 0.70 |
| Fragrance Microcapsules | 1.0 | 1.00 | 1.0 |
| Preservatives, pH adjusters | Up to 1% | Up to 1% | Up to 1% |

[1] Mirapol AT-1, Copolymer of Acrylamide(AM) and TRIQUAT, MW = 1,000,000; CD = 1.6 meq./gram; 10% active; Supplier Rhodia
[2] Jaguar C500, MW - 500,000, CD = 0.7, supplier Rhodia
[3] Mirapol 100S, 31.5% active, supplier Rhodia
[4] Sodium Laureth Sulfate, 28% active, supplier: P&G
[5] Sodium Lauryl Sulfate, 29% active supplier: P&G
[6] Glycidol Silicone VC2231-193C
[7] Tegobetaine F-B, 30% active supplier: Goldschmidt Chemicals
[8] Monamid CMA, 85% active, supplier Goldschmidt Chemical
[9] Ethylene Glycol Distearate, EGDS Pure, supplier Goldschmidt Chemical
[10] Sodium Chloride USP (food grade), supplier Morton; note that salt is an adjustable ingredient, higher or lower levels may be added to achieve target viscosity.

TABLE 7.2

Shampoo Formulations of Examples 7D-7F.

| Ingredient | Example 7D | 7E | 7F |
|---|---|---|---|
| Water | q.s. | q.s. | q.s. |
| Silicone A [1] | 1.0 | 0.5 | 0.5 |
| Cyclopentasiloxane [4] | — | 0.61 | 1.5 |
| Behenyl trimethyl ammonium chloride [5] | 2.25 | 2.25 | 2.25 |
| Isopropyl alcohol | 0.60 | 0.60 | 0.60 |
| Cetyl alcohol [6] | 1.86 | 1.86 | 1.86 |
| Stearyl alcohol [7] | 4.64 | 4.64 | 4.64 |
| Disodium EDTA | 0.13 | 0.13 | 0.13 |
| NaOH | 0.01 | 0.01 | 0.01 |
| Benzyl alcohol | 0.40 | 0.40 | 0.40 |
| Methylchloroisothiazolinone/ Methylisothiazolinone [8] | 0.0005 | 0.0005 | 0.0005 |
| Panthenol [9] | 0.10 | 0.10 | 0.10 |
| Panthenyl ethyl ether [10] | 0.05 | 0.05 | 0.05 |
| Fragrance | 0.35 | 0.35 | 0.35 |
| Fragrance Microcapsules | 1.0 | 1.0 | 1.0 |

[1] Glycidol Silicone
[4] Cyclopentasiloxane: SF1202 available from Momentive Performance Chemicals
[5] Behenyl trimethyl ammonium chloride/Isopropyl alcohol: Genamin TM KMP available from Clariant
[6] Cetyl alcohol: Konol TM series available from Shin Nihon Rika
[7] Stearyl alcohol: Konol TM series available from Shin Nihon Rika
[8] Methylchloroisothiazolinone/Methylisothiazolinone: Kathon TM CG available from Rohm & Haas
[9] Panthenol: Available from Roche
[10] Panthenyl ethyl ether: Available from Roche

TABLE 7.3

Shampoo Formulations of Examples 7G and 7H

| Ingredient | Example 7G | 7H |
|---|---|---|
| Sodium Laureth Sulfate | 10.00 | 10.00 |
| Sodium Lauryl Sulfate | 1.50 | 1.50 |
| Cocamidopropyl betaine | 2.00 | 2.00 |
| Guar Hydroxypropyl trimonium chloride [1] | 0.40 | |
| Guar Hydroxypropyl trimonium chloride [2] | | 0.40 |
| Dimethicone [3] | 2.00 | 2.00 |
| Gel Network [4] | | 27.27 |
| Ethylene Glycol Distearate | 1.50 | 1.50 |
| 5-Chloro-2-methyl-4-isothiazolin-3-one, Kathon CG | 0.0005 | 0.0005 |
| Sodium Benzoate | 0.25 | 0.25 |
| Disodium EDTA | 0.13 | 0.13 |

TABLE 7.3-continued

Shampoo Formulations of Examples 7G and 7H

| Ingredient | Example 7G | 7H |
|---|---|---|
| Perfume | 0.40 | 0.40 |
| Fragrance Microcapsules | 0.30 | 0.30 |
| Citric Acid/Sodium Citrate Dihydrate | pH QS | pH QS |
| Sodium Chloride/Ammonium Xylene Sulfonate | Visc. QS | Visc. QS |
| Water | QS | QS |

[1] Jaguar C17 available from Rhodia
[2] N-Hance 3269 (with Mol. W. of ~500,000 and 0.8 meq/g) available from Aqulaon/Hercules
[3] Viscasil 330M available from General Electric Silicones
[4] Gel Networks; See composition in Table 7.4 below. The water is heated to about 74° C. and the Cetyl Alcohol, Stearyl Alcohol, and the SLES Surfactant are added to it. After incorporation, this mixture is passed through a heat exchanger where it is cooled to about 35° C. As a result of this cooling step, the Fatty Alcohols and surfactant crystallized to form a crystalline gel network.

TABLE 7.4

Gel Network Composition

| Ingredient | Wt. % |
|---|---|
| Water | 86.14% |
| Cetyl Alcohol | 3.46% |
| Stearyl Alcohol | 6.44% |
| Sodium laureth-3 sulfate (28% Active) | 3.93% |
| 5-Chloro-2-methyl-4-isothiazolin-3-one, Kathon CG | 0.03% |

Example 8—Lotion

For the examples shown in Table 8 below, in a suitable container, combine the ingredients of Phase A. In a separate suitable container, combine the ingredients of Phase B. Heat each phase to 73° C.-78° C. while mixing each phase using a suitable mixer (e.g., Anchor blade, propeller blade, or IKA T25) until each reaches a substantially constant desired temperature and is homogenous. Slowly add Phase B to Phase A while continuing to mix Phase A. Continue mixing until batch is uniform. Pour product into suitable containers at 73-78° C. and store at room temperature. Alternatively, continuing to stir the mixture as temperature decreases results in lower observed hardness values at 21 and 33° C.

TABLE 8

Lotion Formulations (Examples 8A-8C).

| Ingredient/Property | Example 8A | 8B | 8C |
|---|---|---|---|
| PHASE A | | | |
| DC-9040 [1] | 8.60 | 3.00 | 5.00 |
| Dimethicone | 4.09 | 4.00 | 4.00 |
| Polymethylsilsesquioxane [2] | 4.09 | 4.00 | 4.00 |
| Cyclomethicone | 11.43 | 0.50 | 11.33 |
| KSG-210 [3] | 5.37 | 5.25 | 5.40 |
| Polyethylene wax [4] | 3.54 | | 2.05 |
| DC-2503 Cosmetic Wax [5] | 7.08 | 10.00 | 3.77 |
| Hydrophobic $TiO_2$ | | | 0.50 |
| Iron oxide coated Mica | | | 0.65 |
| $TiO_2$ Coated Mica | 1.00 | 1.00 | |
| Fragrance Microcapsules | 1.00 | 1.00 | 1.00 |
| PHASE B | | | |
| Glycerin | 10.00 | 10.00 | 10.00 |
| Dexpanthenol | 0.50 | 0.50 | 0.50 |

TABLE 8-continued

| Lotion Formulations (Examples 8A-8C). | | | |
|---|---|---|---|
| | Example | | |
| Ingredient/Property | 8A | 8B | 8C |
| Pentylene Glycol | 3.00 | 3.00 | 3.00 |
| Hexamidine Diisethionate [6] | 0.10 | 0.10 | 0.10 |
| Niacinamide [7] | 5.00 | 5.00 | 5.00 |
| Methylparaben | 0.20 | 0.20 | 0.20 |
| Ethylparaben | 0.05 | 0.05 | 0.05 |
| Sodium Citrate | 0.20 | 0.20 | 0.20 |
| Citric Acid | 0.03 | 0.03 | 0.03 |
| Sodium Benzoate | 0.05 | 0.05 | 0.05 |
| Sodium Chloride | 0.50 | 0.50 | 0.50 |
| FD&C Red #40 (1%) | 0.05 | 0.05 | 0.05 |
| Water | q.s to 100 | q.s to 100 | q.s to 100 |
| Hardness at 21° C. (g) | 33.3 | 15.4 | 14.2 |
| Hardness at 33° C. (g) | 6.4 | 0.7 | 4.0 |

[1] 12.5% Dimethicone Crosspolymer in Cyclopentasiloxane. Available from Dow Corning.
[2] E.g., TOSPEAR 145A or TOSPEARL 2000. Available from GE Toshiba Silicon.
[3] 25% Dimethicone PEG-10/15 Crosspolymer in Dimethicone. Available from Shin-Etsu.
[4] JEENATE 3H polyethylene wax from Jeen.
[5] Stearyl Dimethicone. Available from Dow Corning.
[6] Hexamidine diisethionate, available from Laboratoires Serobiologiques.
[7] Additionally or alternatively, the composition may comprise one or more other skin care actives, their salts and derivatives, as disclosed herein, in amounts also disclosed herein as would be deemed suitable by one of skill in the art.

Example 9—Antiperspirant/Deodorant

Example 9A of Table 9.1 below can be made via the following general process, which one skilled in the art will be able to alter to incorporate available equipment. The ingredients of Part I and Part II are mixed in separate suitable containers. Part II is then added slowly to Part I under agitation to assure the making of a water-in-silicone emulsion. The emulsion is then milled with a suitable mill, for example a Greeco 1L03 from Greeco Corp., to create a homogenous emulsion. Part III is mixed and heated to 88° C. until the all solids are completely melted. The emulsion is then also heated to 88° C. and then added to the Part 3 ingredients. The final mixture is then poured into an appropriate container, and allowed to solidify and cool to ambient temperature.

TABLE 9.1

| Antiperspirant/Deodorant Formulation (Example 9A). | |
|---|---|
| Ingredient | Example 9A |
| Part I: Partial Continuous Phase | |
| Hexamethyldisiloxane[1] | QS |
| DC5200[2] | 1.20 |
| Fragrance | 0.35 |
| Fragrance Capsules | 1.00 |
| Part II: Disperse Phase | |
| ACH (40% solution)[3] | 40.00 |
| propylene glycol | 5.00 |
| Water | 12.30 |
| Part III: Structurant Plus Remainder of Continuous Phase | |
| FINSOLVE TN | 6.50 |

QS—indicates that this material is used to bring the total to 100%.
[1]DC 246 fluid from Dow Corning
[2]from Dow Corning
[3]Standard aluminum chlorohydrate solution Examples 9B to 9E of Table 9.2 below can be made as follows: all ingredients except the fragrance, and fragrance capsules are combined in a suitable container and heated to about 85° C. to form a homogenous liquid. The solution is then cooled to about 62° C. and then the fragrance, and fragrance microcapsules are added. The mixture is then poured into an appropriate container and allowed to solidify up cooling to ambient temperature.

Example 9F of Table 9.2 can be made as follows: all the ingredients except the propellant are combined in an appropriate aerosol container. The container is then sealed with an appropriate aerosol delivery valve. Next air in the container is removed by applying a vacuum to the valve and then propellant is added to container through the valve. Finally an appropriate actuator is connected to the valve to allow dispensing of the product.

TABLE 9.2

| Antiperspirant/Deodorant Formulations | | | | | |
|---|---|---|---|---|---|
| | Example | | | | |
| Ingredient | 9B | 9C | 9D | 9E | 9F |
| Product Form | Solid De-odorant | Solid De-odorant | Solid De-odorant | Solid De-odorant | Deodorant or Body Spray |
| dipropylene glycol | 45 | 22 | 20 | 30 | 20 |
| propylene glycol | 22 | 45 | 22 | | |
| tripopylene glycol | | | 25 | | |
| Glycerine | | | | 10 | |
| PEG -8 | | | | 20 | |
| ethanol | | | | | QS |
| Water | QS | QS | QS | QS | |
| sodium stearate | 5.5 | 5.5 | 5.5 | 5.5 | |
| tetra sodium EDTA | 0.05 | 0.05 | 0.05 | 0.05 | |
| sodium hydroxide | 0.04 | 0.04 | 0.04 | 0.04 | |
| triclosan | 0.3 | 0.3 | 0.3 | 0.3 | |
| Fragrance | 0.5 | 0.5 | 0.5 | 0.5 | 0.5 |
| Fragrance capsules | 1.0 | 1.0 | 1.0 | 1.0 | 0.5 |
| Propellant (1,1 difluoroethane) | | | | | 40 |

QS—indicates that this material is used to bring the total to 100%.

Example 10—Rinse-Off Conditioner

The conditioning compositions of Examples 10A through 10F of Table 10 are prepared as follows: cationic surfactants, high melting point fatty compounds are added to water with agitation, and heated to about 80° C. The mixture is cooled down to about 50° C. to form a gel matrix carrier. Separately, slurries of perfume microcapsules and silicones are mixed with agitation at room temperature to form a premix. The premix is added to the gel matrix carrier with agitation. If included, other ingredients such as preservatives are added with agitation. Then the compositions are cooled down to room temperature.

The conditioning composition of Example 10B of Table 10 is prepared as follows: cationic surfactants, high melting point fatty compounds are added to water with agitation, and heated to about 80° C. The mixture is cooled down to about 50° C. to form a gel matrix carrier. Then, silicones are added with agitation. Separately, slurries of perfume microcapsules, and if included, other ingredients such as preservatives are added with agitation. Then the compositions are cooled down to room temperature.

TABLE 10

Rinse-Off Conditioner Formulations (Examples 10A-10F).

| Ingredient | Example | | | | | |
|---|---|---|---|---|---|---|
| | 10A | 10B | 10C | 10D | 10E | 10F[3] |
| Premix | | | | | | |
| Aminosilicone-1[1] | 0.50 | 0.50 | | | | |
| Aminosilicone-2[2] | | | 0.50 | 0.50 | 0.50 | |
| PDMS | | | | | | 0.50 |
| Fragrance microcapsules | . . . | 1.0 | 1.0 | 1.0 | 1.0 | 1.0 |
| Gel matrix carrier | | | | | | |
| Behenyl trimethyl ammonium chloride | 2.30 | 2.30 | 2.30 | 2.30 | 2.30 | 2.30 |
| Cetyl alcohol | 1.5 | 1.5 | 1.5 | 1.5 | 1.5 | 1.5 |
| Stearyl alcohol | 3.8 | 3.8 | 3.8 | 3.8 | 3.8 | 3.8 |
| Deionized Water | QS | QS | QS | QS | QS | QS |
| Preservatives | 0.4 | 0.4 | 0.4 | 0.4 | 0.4 | 0.4 |
| Panthenol | — | — | 0.03 | — | — | — |
| Panthenyl ethyl ether | — | — | 0.03 | — | — | — |

[1]Aminosilicone-1 (AMD): having an amine content of 0.12-0.15 m mol/g and a viscosity of 3,000-8,000 mPa · s, which is water insoluble

[2] Aminosilicone-2 (TAS): having an amine content of 0.04-0.06 m mol/g and a viscosity of 10,000-16,000 mPa · s, which is water insoluble

[3]Comparative example with PDMS instead of amino silicone

Example 11—Body Cleansing Composition

The body cleaning compositions of Examples 11A-11C are prepared as follows.

The cleansing phase composition is prepared by adding surfactants, guars, and Stabylen 30 to water. Sodium chloride is then added to the mixture to thicken the cleansing phase composition. Preservatives and chelants are added to the formulation. Finally, perfume is added to the suspension.

The benefit phase composition is prepared by mixing petrolatum and mineral oil to make a homogeneous mixture. Fragrance microcapsules are added to the suspension. Finally, the cleansing phase (e.g. surfactant phase) and benefit phase are mixed in different ratios to yield the body cleansing composition.

TABLE 11

Body Cleansing Composition Formulations (Examples 11A-11C).

| Ingredient | Example | | |
|---|---|---|---|
| | 11A | 11B | 11C |
| I: Cleansing Phase Composition | | | |
| Sodium Trideceth Sulfate (sulfated from Iconol TDA-3 (BASF Corp.) to >95% sulfate) | 5.9 | 5.9 | 5.9 |
| Sodium Lauryl Sulfate | 5.9 | 5.9 | 5.9 |
| Sodium Lauroamphoacetate (Cognis Chemical Corp.,) | 3.6 | 3.6 | 3.6 |
| Guar Hydroxypropyltrimonium Chloride (N-Hance 3196 from Aqualon) | — | 0.3 | 0.7 |
| Guar Hydroxypropyltrimonium Chloride (Jaguar C-17 from Rhodia) | 0.6 | — | — |
| Stabylen 30 (Acrylates/Vinyl Isodecanoate, 3V) | 0.33 | 0.33 | 0.33 |
| Sodium Chloride | 3.75 | 3.75 | 3.75 |
| Trideceth-3 (Iconal TDA-3 from BASF Corp.) | 1.75 | 1.75 | 1.75 |
| Methyl chloro isothiazolinone and methyl isothiazolinone (Kathon CG, Rohm & Haas) | 0.033 | 0.033 | 0.033 |
| EDTA (Dissolvine NA 2x) | 0.15 | 0.15 | 0.15 |

TABLE 11-continued

Body Cleansing Composition Formulations (Examples 11A-11C).

| Ingredient | Example | | |
|---|---|---|---|
| | 11A | 11B | 11C |
| Sodium Benzoate | 0.2 | 0.2 | 0.2 |
| Citric Acid, titrate | pH = 5.7 ± 0.2 | pH = 5.7 ± 0.2 | pH = 5.7 ± 0.2 |
| Perfume | 1.11% | 1.11% | 1.11% |
| Water and Minors (NaOH) | Q.S. | Q.S. | Q.S. |
| II: Benefit Phase Composition | | | |
| Petrolatum (G2218 from Sonnerbonn) | 60 | 60 | 60 |
| Mineral Oil (Hydrobrite 1000 from Sonnerbonn) | 20 | 20 | 20 |
| Fragrance Microcapsules | 10 | 10 | 10 |
| III: Surfactant Phase:Benefit Phase Blending Ratio | 50:50 | 90:10 | 90:10 |

Example 12—Fabric Softening Product

Non-limiting examples of product formulations containing purified perfume microcapsules of the aforementioned examples are summarized in the following table.

TABLE 12

| Fabric Softening Product Formulations (Examples 12A-12J). | | | | | | | | | | |
|---|---|---|---|---|---|---|---|---|---|---|
| | Example | | | | | | | | | |
| Ingredient | 12A | 12B | 12C | 12D | 12E | 12F | 12G | 12H | 12I | 12J |
| FSA [a] | 14 | 16.47 | 14 | 12 | 12 | 16.47 | 3.00 | 6.5 | 5 | 5 |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Microcapsule (% active)* | 0.6 | 0.75 | 0.6 | 0.75 | 0.37 | 0.60 | 0.37 | 0.6 | 0.37 | 0.37 |
| Phase Stabilizing Polymer [f] | 0.21 | 0.25 | 0.21 | 0.21 | 0.14 | — | — | 0.14 | — | — |
| Suds Suppressor [g] | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA [h] | 0.017 | 0.017 | 0.017 | 0.017 | 0.007 | 0.007 | 0.20 | — | 0.002 | 0.002 |
| Preservative (ppm) [i, j] | 5 | 5 | 5 | 5 | 5 | 5 | — | 250 [j] | 5 | 5 |
| Antifoam[k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant[l] | 0.01 | 0.01 | 0.01 | 0.01 | 0.01 | 0.01 | 0.01 | 0.01 | 0.01 | 0.01 |
| Neat Unencapsulated Perfume | 0.8 | 0.7 | 0.9 | 0.5 | 1.2 | 0.5 | 1.1 | 0.6 | 1.0 | 0.9 |
| Deionized Water | Balance | Balance | Balance | Balance | Balance | Balance | Balance | Balance | Balance | Balance |

[a] N,N-di(tallowoyloxyethyl)-N,N-dimethylammonium chloride.

[f] Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.

[g] SE39 from Wacker

[h] Diethylenetriaminepentaacetic acid.

[i] KATHON CG available from Rohm and Haas Co. "PPM" is "parts per million."

[j] Gluteraldehyde

[k]Silicone antifoam agent available from Dow Corning Corp. under the trade name DC2310.

[l]Hydrophobically-modified ethoxylated urethane available from Rohm and Haas under the tradename Aculyn ™ 44.

*Suitable microcapsules provided in Examples 2. (Percent active relates to the core content of the microcapsule)

Example 13—Dry Laundry Formulations

Non-limiting examples of product formulations containing purified perfume microcapsules of the aforementioned examples are summarized in the following table.

TABLE 13

| Dry Laundry Formulations (Examples 13A-13G) | | | | | | | |
|---|---|---|---|---|---|---|---|
| | % w/w granular laundry detergent composition Example | | | | | | |
| Ingredient | 13A | 13B | 13C | 13D | 13E | 13F | 13G |
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphonic acid) | 0.4 | 0.4 | 0.4 | 0.4 | 0.4 | 0.4 | 0.4 |
| Mono-$C_{12-14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | QS | QS | QS | QS | QS | QS | QS |

TABLE 13-continued

| Dry Laundry Formulations (Examples 13A-13G) | | | | | | | |
|---|---|---|---|---|---|---|---|
| | % w/w granular laundry detergent composition Example | | | | | | |
| Ingredient | 13A | 13B | 13C | 13D | 13E | 13F | 13G |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt. % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt. % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Perfume oil | 0.5 | 0.5 | 0.5 | 0.5 | 0.5 | 0.5 | 0.5 |
| Solid perfume particles | 0.4 | 0 | 0.4 | 0.4 | 0.4 | 0.4 | 0.6 |
| Spray Dried Perfume microcapsules (Example 4) | 1.3 | 2.4 | 1 | 1.3 | 1.3 | 1.3 | 0.7 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

QS—as used herein indicates that this material is used to bring the total to 100%.

Example 14—Liquid Laundry Formulations (HDLs)

Non-limiting examples of product formulations containing purified perfume microcapsules of the aforementioned examples are summarized in Tables 14.1, 14.2 and 14.3 below.

TABLE 14.1

| Liquid Laundry Formulations (HDLs) | | | | | | |
|---|---|---|---|---|---|---|
| | Example | | | | | |
| Ingredient | 14A | 14B | 14C | 14D | 14E | 14F |
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine pentamethylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |

TABLE 14.1-continued

| Liquid Laundry Formulations (HDLs) | | | | | | |
|---|---|---|---|---|---|---|
| | Example | | | | | |
| Ingredient | 14A | 14B | 14C | 14D | 14E | 14F |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Perfume | 0.7 | 0.5 | 0.8 | 0.8 | 0.6 | 0.6 |
| Polyethyleneimine | 0.01 | 0.10 | 0.00 | 0.10 | 0.20 | 0.05 |
| Spray Dried Perfume Microcapsules of Example 4 | 1.00 | 5.00 | 1.00 | 2.00 | 0.10 | 0.80 |
| Water | Balance to 100% | Balance to 100% | Balance to 100% | Balance to 100% | Balance to 100% | Balance to 100% |

TABLE 14.2

| Liquid Laundry Detergent Formulations | | | | |
|---|---|---|---|---|
| | Example | | | |
| Ingredient | 14G | 14H | 14I | 14J |
| C14-C15 alkyl poly ethoxylate (8) | 6.25 | 4.00 | 6.25 | 6.25 |
| C12-C14 alkyl poly ethoxylate (7) | 0.40 | 0.30 | 0.40 | 0.40 |
| C12-C14 alkyl poly ethoxylate (3) sulfate Na salt | 10.60 | 6.78 | 10.60 | 10.60 |
| Linear Alkylbenzene sulfonate acid | 0.19 | 1.16 | 0.79 | 0.79 |
| Citric Acid | 3.75 | 2.40 | 3.75 | 3.75 |
| C12-C18 Fatty Acid | 4.00 | 2.56 | 7.02 | 7.02 |
| Enzymes | 0.60 | 0.4 | 0.60 | 0.60 |
| Boric Acid | 2.4 | 1.5 | 1.25 | 1.25 |
| Trans-sulphated ethoxylated hexamethylene diamine quat | 1.11 | 0.71 | 1.11 | 1.11 |
| Diethylene triamine penta methylene phosphonic acid | 0.17 | 0.11 | 0.17 | 0.17 |
| Fluorescent brightener | 0.09 | 0.06 | 0.14 | 0.14 |
| Hydrogenated Castor Oil | 0.05 | 0.300 | 0.20 | 0.20 |
| Ethanol | 2.50 | 1.00 | 2.50 | 2.50 |
| 1,2 propanediol | 1.14 | 0.7 | 1.14 | 1.14 |
| Sodium hydroxide | 3.8 | 2.6 | 4.60 | 4.60 |
| Mono Ethanol Amine | 0.8 | 0.5 | | |
| Na Cumene Sulphonate | | | 1.0 | |
| Dye | 0.002 | 0.002 | 0.002 | 0.002 |
| Opacifier (Styrene Acrylate based) | 0.1 | | | |
| Bentonite Softening Clay | | 1.0 | | |
| Polyquaternium 10 - Cationic hydroxyl ethyl cellulose | 1.0 | | 1.0 | 1.0 |
| PP-5495 (silicone ex Dow Corning Corporation, Midland, MI) | | 1.0 | | |
| DC 1664 (silicone ex Dow Corning Corporation, Midland, MI) | | | 1.0 | |
| Spray Dried Perfume micro capsules of Example 4 | 0.8 | 0.5 | 1.0 | 0.7 |
| Perfume | 0.7 | 0.55 | 1.00 | 1.00 |
| Poly Ethylene Imine MW 25000 | 0.1 | | | |
| Water | Up to 100 | Up to 100 | Up to 100 | Up to 100 |

TABLE 14.3

| Liquid Laundry Detergent Formulations. | | | |
|---|---|---|---|
| | Example | | |
| Ingredient | 14K | 14L | 14M |
| C14-C15 alkyl poly ethoxylate (8) | 3.7 | | 20.7 |
| C12-C14 alkyl poly ethoxylate (7) | | 16.7 | |
| C12-C14 alkyl poly ethoxylate (3) sulfate Na salt | 17.8 | | 5.5 |
| Linear Alkylbenzene sulfonate acid | 12.5 | 22.9 | 13.5 |
| Citric Acid | 3.9 | | 1.7 |
| C12-C18 Fatty Acid | 11.1 | 18 | 5.1 |
| Enzymes | 3 | 1.2 | 3 |
| Boric Acid | 0.5 | | 0.5 |
| Trans-sulphated ethoxylated hexamethylene diamine quat | 3.25 | | 1.2 |
| PEI 600 EO20 | 1.25 | | 1.2 |
| Diethylene triamine penta methylene phosphonic acid or HEDP | 1.6 | | 0.85 |
| Fluorescent brightener | 0.2 | 0.3 | 0.14 |
| Hydrogenated Castor Oil | | 0.2 | |
| 1,2 propanediol | 4.3 | 20.3 | 11.7 |
| Sodium hydroxide | | 1.0 | 3.9 |
| Mono Ethanol Amine | 9.8 | 6.8 | 3.1 |
| Dye | Present | Present | Present |
| PDMS | | 2.15 | |
| Potassium sulphite | | 0.2 | |
| Spray Dried Perfume microcapsules of Examples 4 | 1.6 | 1.5 | 1.4 |
| Perfume | 1.2 | 1.6 | 1.0 |
| Form. Phenyl Boronic Acid | | | Present |
| Water** | Up to 100 | Up to 100 | Up to 100 |

**Low water liquid detergent in Polyvinylalcohol unidose/sachet

Example 15—Liquid and Gel Detergents

Non-limiting examples of product formulations containing purified perfume microcapsules of the aforementioned examples are summarized in Table 15 below.

TABLE 15

Liquid and Gel Detergent Formulations (% by Weight)

| Ingredient | Example 15A | 15B | 15C |
|---|---|---|---|
| Alkylbenzenesulfonic acid | 17.2 | 12.2 | 23 |
| C12-14 alcohol 7-ethoxylate | 8.6 | 0.4 | 19.5 |
| C14-15 alcohol 8-ethoxylate | — | 9.6 | — |
| C12-14 alcohol 3-ethoxylate sulphate, Na salt | 8.6 | — | — |
| C8-10 Alkylamidopropyldimethyl amine | — | — | 0.9 |
| Citric acid | 2.9 | 4.0 | — |
| C12-18 fatty acid | 12.7 | 4.0 | 17.3 |
| Enzymes | 3.5 | 1.1 | 1.4 |
| Ethoxylated polyimine | 1.4 | — | 1.6 |
| Ethoxylated polyimine polymer, quaternized and sulphated | 3.7 | 1.8 | 1.6 |
| Hydroxyethane diphosphonic acids (HEDP) | 1.4 | — | — |
| Pentamethylene triamine pentaphosphonic acid | — | 0.3 | — |
| Catechol 2,5 disulfonate, Na salt | 0.9 | — | — |
| Fluorescent whitening agent | 0.3 | 0.15 | 0.3 |
| 1,2 propandiol | 3.5 | 3.3 | 22 |
| Ethanol | — | 1.4 | — |
| Diethylene glycol | — | 1.6 | — |
| 1-ethoxypentanol | 0.9 | — | — |
| Sodium cumene sulfonate | | 0.5 | — |
| Monoethanolamine (MEA) | 10.2 | 0.8 | 8.0 |
| MEA borate | 0.5 | 2.4 | — |
| Sodium hydroxide | — | 4.6 | — |
| Perfume | 1.6 | 0.7 | 1.5 |
| Spray Dried Perfume microcapsules of Example 4 | 1.1 | 1.2 | 0.9 |
| Water | 22.1 | 50.8 | 2.9 |
| Perfume, dyes, miscellaneous minors | Balance | Balance | Balance |
| Undiluted viscosity ($V_n$) at 20 $s^{-1}$, cps | 2700 | 400 | 300 |

Example 16—Liquid Unit Dose

The following are examples of unit dosage forms wherein the liquid composition is enclosed within a PVA film. The preferred film used in the present examples is Monosol M8630 76 μm thickness.

TABLE 16

Unit Dose Laundry Cleaner

| | Example | | | | | | | |
|---|---|---|---|---|---|---|---|---|
| | 16A 3 compartments | | | 16B 2 compartments Compartment # | | 16C 3 compartments | | |
| | 42 | 43 | 44 | 45 | 46 | 47 | 48 | 49 |
| | Dosage (g) | | | | | | | |
| | 34.0 | 3.5 | 3.5 | 30.0 | 5.0 | 25.0 | 1.5 | 4.0 |
| Ingredients | Weight % | | | | | | | |
| Alkylbenzene sulfonic acid | 20.0 | 20.0 | 20.0 | 10.0 | 20.0 | 20.0 | 25 | 30 |
| Alkyl sulfate | | | | 2.0 | | | | |
| $C_{12-14}$ alkyl 7-ethoxylate | 17.0 | 17.0 | 17.0 | | 17.0 | 17.0 | 15 | 10 |
| $C_{12-14}$ alkyl ethoxy 3 sulfate | 7.5 | 7.5 | 7.5 | | | 7.5 | 7.5 | |
| Citric acid | 0.5 | | 2.0 | 1.0 | | | | 2.0 |
| Zeolite A | | | | 10.0 | | | | |
| $C_{12-18}$ Fatty acid | 13.0 | 13.0 | 13.0 | | 18.0 | 18.0 | 10 | 15 |
| Sodium citrate | | | | 4.0 | 2.5 | | | |
| Enzymes | 0-3 | 0-3 | 0-3 | 0-3 | | 0-3 | 0-3 | 0-3 |
| Sodium Percarbonate | | | | 11.0 | | | | |
| TAED | | | | 4.0 | | | | |
| Polycarboxylate | | | | 1.0 | | | | |
| Ethoxylated Polyethylenimine[1] | 2.2 | 2.2 | 2.2 | | | | | |
| Hydroxyethane diphosphonic acid | 0.6 | 0.6 | 0.6 | 0.5 | | | 2.2 | |
| Ethylene diamine tetra(methylene phosphonic) acid | | | | | | 0.4 | | |
| Brightener | 0.2 | 0.2 | 0.2 | 0.3 | | 0.3 | | |
| Spray Dried Microcapsules of examples 4 | 0.4 | 1.2 | 1.5 | 1.3 | 1.3 | 0.4 | 0.12 | 0.2 |
| Water | 9 | 8.5 | 10 | 5 | 11 | 10 | 10 | 9 |
| CaCl2 | | | | | | | 0.01 | |
| Perfume | 1.7 | 1.7 | | 0.6 | | 1.5 | 0.5 | |
| Minors (antioxidant, sulfite, aesthetics, . . . ) | 2.0 | 2.0 | 2.0 | 4.0 | 1.5 | 2.2 | 2.2 | 2.0 |
| Buffers (sodium carbonate, monoethanolamine) [2] | To pH 8.0 for liquids To RA > 5.0 for powders | | | | | | | |
| Solvents (1,2 propanediol, ethanol), sodium sulfate | To 100 p | | | | | | | |

[1]Polyethylenimine (MW = 600) with 20 ethoxylate groups per —NH.

[2] RA = Reserve Alkalinity (g NaOH/dose)

Example 17. Scent Booster

Microcapsules can also be incorporated into a laundry scent booster. Exemplary scent booster formulations are presented in Table 17.1, 17.2, and 17.3

TABLE 17.1

| Material | Parts |
|---|---|
| Urea beads | 86 |
| Bentonite | 3 |
| Perfume oil | 3 |
| Spray Dried Microcapsules of Example 3 | 8 |

Powders are mixed together using a low shear powder blender.

TABLE 17.2

| Material | Parts |
|---|---|
| Sodium Chloride powder | 95 |
| Spray Dried Microcapsules of Example 3 | 5 |

Powders are mixed together using a low shear powder blender.

TABLE 17.3

| Material | Parts |
|---|---|
| Polyethylene Glycol 8000 | 87 |
| Dipropylene Glycol | 1.8 |
| Perfume oil | 7.0 |
| Spray Dried Microcapsules of Example 3 | 3.8 |

Polyethylene glycol 8000 is melted at 75 degrees Celsius. The dipropylene glycol and perfume oil are added and mixed to yield a homogeneous mixture. The spray dried microcapsule powder of Example 4 is incorporated into the melt at 60-65° C. and subsequently extruded into pellets or processed using a steel belt to make pastilles. Such pastille processing equipment is available from SBS Steel Belt Systems.

ADDITIONAL NUMBERED EMBODIMENTS OF THE INVENTION

1. A controlled release particle comprising:

a core that comprises at least one hydrophobic active ingredient, optionally a sugar alcohol, and optionally a plasticizer; and a shell that comprises a reaction product of (a) at least one isocyanate resin and at least one epoxy resin with (b) at least one treated protein isolate, at least one mono epoxy alkoxy silane, at least one hydrolyzed organofunctional silane, at least one gelatinized polysaccharide, at least one amino polysaccharide and at least one adduct, wherein the at least one adduct is at least one of:

(i) at least one amine-acid functional urea linked amino acid isocyanate (AAI) adduct having a structure represented by Formula I:

Formula I

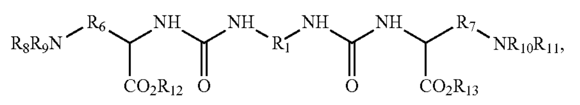

and salts thereof, and (ii) at least one amine-hydroxy-acid functional amino acid epoxide (AAE) adduct having a structure represented by Formula II:

Formula II

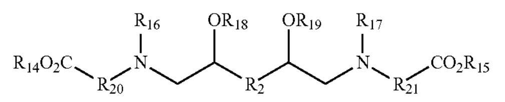

and salts thereof, where $R_1$ is a moiety of a monomer or a prepolymer comprising two —NCO functional groups wherein the NCO functional groups have reacted to form urea linkages;

$R_2$ is a moiety of a monomer or a prepolymer comprising two glycidyl ether epoxide functional groups wherein the epoxide groups have reacted to form amino alcohol groups;

$R_6$, $R_7$, $R_{20}$ and $R_{21}$ are each independently $(CH_2)_n$, wherein n is 1-6;

$R_8$, $R_9$, $R_{10}$ and $R_{11}$ are each independently hydrogen or $CH_2X$;

$R_{12}$ and $R_{13}$ are each independently hydrogen, an alkali metal cation, or X;

$R_{14}$ and $R_{15}$ are each independently hydrogen, an alkali metal cation, or X;

$R_{16}$ and $R_{17}$ are each independently hydrogen or X;

$R_{18}$ and $R_{19}$ are each independently hydrogen, $SiO_3$ or X; and each occurrence of X is independently selected from the group consisting of hydrogen and a substituent.

2. The controlled release particle of embodiment 1, having a biodegradability greater than 60% measured according to OECD 301D.

3. The controlled release particle of embodiment 1 or 2, comprising the at least one AAI adduct, wherein:

$R_6$ and $R_7$ are each $(CH_2)_4$;

$R_8$, $R_9$, $R_{10}$ and $R_{11}$ are each hydrogen; and $R_{12}$ and $R_{13}$ are each independently hydrogen or an alkali metal cation.

4. The controlled release particle of any one of embodiments 1-3, comprising the at least one AAE adduct, wherein:

$R_{14}$ and $R_{15}$ are each independently hydrogen or an alkali metal cation;

$R_{16}$ and $R_{17}$ are each hydrogen;

$R_{18}$ and $R_{19}$ are each independently hydrogen or $SiO_3$; and $R_{20}$ and $R_{21}$ are each $(CH_2)_2$.

5. The controlled release particle of any one of embodiments 1-4, wherein the shell comprises a polymer comprising more than one of the at least one AAI adduct or more than one of the at least one AAE adduct.

6. The controlled release particle of any one of embodiments 1-5, wherein the shell comprises a copolymer comprising at least one of the AAI adduct and at least one of the AAE adduct.

7. The controlled release particle of any one of embodiments 1-6, wherein the core comprises the sugar alcohol, which is an alcohol of a monosaccharide, disaccharide, trisaccharide, tetra-saccharide or penta-saccharide.

8. The controlled release particle of any one of embodiments 1-7, wherein the core comprises the plasticizer, which is a member selected from the group consisting of methyl esters of rosin, polyazelate esters, di-fatty acid esters, citrate esters, polyadipate esters and polyester resins consisting of inner and intra-esters of polyhydroxy carboxylic acids.

9. The controlled release particle of any one of embodiments 1-8, wherein the hydrophobic active ingredient is a member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

10. The controlled release particle of any one of embodiments 1-9, wherein the at least one treated protein isolate is a member selected from the group consisting of proteinogenic L-amino acids, animal protein, plant protein, animal protein hydrolysate, plant protein hydrolysate, animal protein produced by physicochemical or fermentative or enzymatic treatment, and plant protein produced by physicochemical or fermentative or enzymatic treatment.

11. The controlled release particle of any one of embodiments 1-10, wherein the at least one mono epoxy alkoxy silane is a member selected from the group consisting of alkoxylated silane, trialkoxy silanes, functionalized trialkoxysilanes, tetraalkoxylated silanes, 1,2-bis(triethoxysilyl)ethane and glycidoxyalkyltrialkoxy.

12. The controlled release particle of any one of embodiments 1-11, wherein the at least one hydrolyzed organofunctional silane is a member selected from the group consisting of hydrolyzed alkoxylated silanes, hydrolyzed trialkoxy silanes, hydrolyzed tetraalkoxylated silanes, and hydrolyzed glycidyl ether silanes.

13. The controlled release particle of any one of embodiments 1-12, wherein the at least one gelatinized polysaccharide is a member selected from the group consisting of tapioca, potato, corn, rice, wheat, carboxy modified polysaccharide, waxy maize starch, pre-gelatinized starch, pregelatinized polysaccharide, pre-gelatinized waxy maize starch, octenyl succinic anhydride modified starch, anionically modified starch and cationically modified starch.

14. The controlled release particle of any one of embodiments 1-13, wherein the at least one amino polysaccharide is a member selected from the group consisting of amino polysaccharide (chitosan), chitosan oligosaccharide and carboxymethyl chitosan.

15. The controlled release particle of any one of embodiments 1-14, having a diameter of 1-150 μm.

16. A controlled release composition comprising more than one said controlled release particle of any one of embodiments 1-15, wherein the controlled release composition is a consumer product selected from the group consisting of a powdered food product, a fluid food product, a powdered nutritional supplement, a fluid nutritional supplement, a fluid fabric enhancer, a solid fabric enhancer, a fluid shampoo, a solid shampoo, a hair conditioner, a body wash, a solid antiperspirant, a fluid antiperspirant, a solid deodorant, a fluid deodorant, a fluid detergent, a solid detergent, a fluid hard surface cleaner, a solid hard surface cleaner, a fluid fabric refresher spray, a diaper, an air freshening product, a nutraceutical supplement, a controlled release fertilizer, a controlled release insecticide, a controlled release dye and a unit dose detergent further comprising a detergent and a water soluble outer film.

17. A method of making the controlled release particle of any one of embodiments 1-16, said method comprising the steps of:

(a) preparing a core material phase by mixing at least one hydrophobic active material with at least one isocyanate resin or prepolymer, at least one epoxy resin or prepolymer, a glycidyloxy alkyl trialkoxy silane, a sugar alcohol and a polymeric plasticizer to make a solution or suspension;

(b) preparing a homogeneous aqueous solution or aqueous dispersion of at least one emulsifier or surfactant and treated protein isolate solution or dispersion;

(c) adding the core material phase into the homogeneous aqueous solution or aqueous dispersion to prepare an oil-in-water emulsion at 20-35° C.;

(d) adjusting a pH and heating the oil-in-water emulsion at 35-40° C. to form a preformed capsule slurry via interfacial polymerization;

(e) adding an aqueous solution of at least one of the at least one AAI adduct, and the at least one AAE adduct into the preformed capsule slurry to form an emulsion;

(f) heating the emulsion to a temperature from 40-60° C. for further polymerization onto a preformed capsule membrane;

(g) adding tetrahydroxy orthosiloxane or orthosilicic acid to the preformed capsule membrane for further cross-linking or polymerization to provide a capsule;

(h) adding a fine powder of amino polysaccharide to form a coacervate on a surface of the capsule;

(i) adding an aqueous dispersion of treated or gelatinized polysaccharide to the capsule to provide a capsule slurry;

(j) optionally, adding preservative into the capsule slurry; and (k) spray drying the capsule slurry to obtain dry powder.

18. The method of embodiment 17, wherein the at least one emulsifier is a member selected from the group consisting of natural gum, polyvinyl pyrrolidone, copolymer of polyvinyl pyrrolidone with vinyl acetate, vinyl alcohol, vinyl imidazole, polyglycerol oleate, polyvinyl alcohol, ethoxylate nonylphenol, secondary alcohol ethoxylate, water soluble protein, modified polysaccharide, Pickering emulsion stabilizer and chitosan.

While the invention has been described in detail and with reference to specific examples thereof, it will be apparent to one skilled in the art that various changes and modifications can be made therein without departing from the spirit and scope thereof.

What is claimed is:

1. A controlled release particle comprising:

a core that comprises at least one hydrophobic active ingredient, optionally a sugar alcohol, and optionally a plasticizer; and a shell that comprises a reaction product of (a) at least one isocyanate resin and at least one epoxy resin with (b) at least one treated protein isolate, at least one mono epoxy alkoxy silane, at least one hydrolyzed organofunctional silane, at least one gelatinized polysaccharide, at least one amino polysaccharide and at least one adduct, wherein the at least one adduct is at least one of:

(i) at least one amine-acid functional urea linked amino acid isocyanate (AAI) adduct having a structure represented by Formula I:

Formula I

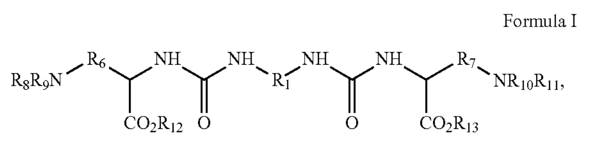

and salts thereof, and (ii) at least one amine-hydroxy-acid functional amino acid epoxide (AAE) adduct having a structure represented by Formula II:

Formula II

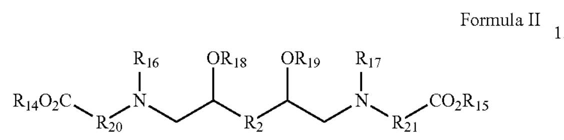

and salts thereof, where $R_1$ is a moiety of a monomer or a prepolymer comprising two —NCO functional groups wherein the NCO functional groups have reacted to form urea linkages;

$R_2$ is a moiety of a monomer or a prepolymer comprising two glycidyl ether epoxide functional groups wherein the epoxide groups have reacted to form amino alcohol groups;

$R_6$, $R_7$, $R_{20}$ and $R_{21}$ are each independently $(CH_2)_n$, wherein n is 1-6;

$R_8$, $R_9$, $R_{10}$ and $R_{11}$ are each independently hydrogen or $CH_2X$;

$R_{12}$ and $R_{13}$ are each independently hydrogen, an alkali metal cation, or X;

$R_{14}$ and $R_{15}$ are each independently hydrogen, an alkali metal cation, or X;

$R_{16}$ and $R_{17}$ are each independently hydrogen or X;

$R_{18}$ and $R_{19}$ are each independently hydrogen, $SiO_3$ or X; and each occurrence of X is independently selected from the group consisting of hydrogen and a substituent.

2. The controlled release particle of claim 1, having a biodegradability greater than 60% measured according to OECD 301D.

3. The controlled release particle of claim 2, comprising the at least one AAI adduct, wherein:

$R_6$ and $R_7$ are each $(CH_2)_4$;

$R_8$, $R_9$, $R_{10}$ and $R_{11}$ are each hydrogen; and $R_{12}$ and $R_{13}$ are each independently hydrogen or an alkali metal cation.

4. The controlled release particle of claim 2, comprising the at least one AAE adduct, wherein:

$R_{14}$ and $R_{15}$ are each independently hydrogen or an alkali metal cation;

$R_{16}$ and $R_{17}$ are each hydrogen;

$R_{18}$ and $R_{19}$ are each independently hydrogen or $SiO_3$; and $R_{20}$ and $R_{21}$ are each $(CH_2)_2$.

5. The controlled release particle of claim 2, wherein the shell comprises a polymer comprising more than one of the at least one AAI adduct or more than one of the at least one AAE adduct.

6. The controlled release particle of claim 2, wherein the shell comprises a copolymer comprising at least one of the AAI adduct and at least one of the AAE adduct.

7. The controlled release particle of claim 2, wherein the core comprises the sugar alcohol, which is an alcohol of a monosaccharide, disaccharide, trisaccharide, tetra-saccharide or penta-saccharide.

8. The controlled release particle of claim 2, wherein the core comprises the plasticizer, which is a member selected from the group consisting of methyl esters of rosin, polyazelate esters, di-fatty acid esters, citrate esters, polyadipate esters and polyester resins consisting of inner and intra-esters of polyhydroxy carboxylic acids.

9. The controlled release particle of claim 2, wherein the hydrophobic active ingredient is a member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

10. The controlled release particle of claim 2, wherein the at least one treated protein isolate is a member selected from the group consisting of proteinogenic L-amino acids, animal protein, plant protein, animal protein hydrolysate, plant protein hydrolysate, animal protein produced by physicochemical or fermentative or enzymatic treatment, and plant protein produced by physicochemical or fermentative or enzymatic treatment.

11. The controlled release particle of claim 2, wherein the at least one mono epoxy alkoxy silane is a member selected from the group consisting of alkoxylated silane, trialkoxy silanes, functionalized trialkoxysilanes, tetraalkoxylated silanes, 1,2-bis(triethoxysilyl)ethane and glycidoxyalkyltrialkoxy.

12. The controlled release particle of claim 2, wherein the at least one hydrolyzed organofunctional silane is a member selected from the group consisting of hydrolyzed alkoxylated silanes, hydrolyzed trialkoxy silanes, hydrolyzed tetraalkoxylated silanes, and hydrolyzed glycidyl ether silanes.

13. The controlled release particle of claim 2, wherein the at least one gelatinized polysaccharide is a member selected from the group consisting of tapioca, potato, corn, rice, wheat, carboxy modified polysaccharide, waxy maize starch, pre-gelatinized starch, pregelatinized polysaccharide, pre-gelatinized waxy maize starch, octenyl succinic anhydride modified starch, anionically modified starch and cationically modified starch.

14. The controlled release particle of claim 2, wherein the at least one amino polysaccharide is a member selected from the group consisting of amino polysaccharide (chitosan), chitosan oligosaccharide and carboxymethyl chitosan.

15. The controlled release particle of claim 2, having a diameter of 1-150 μm.

16. A controlled release composition comprising more than one said controlled release particle of claim 2, wherein the controlled release composition is a consumer product selected from the group consisting of a powdered food product, a fluid food product, a powdered nutritional supplement, a fluid nutritional supplement, a fluid fabric enhancer, a solid fabric enhancer, a fluid shampoo, a solid shampoo, a hair conditioner, a body wash, a solid antiperspirant, a fluid antiperspirant, a solid deodorant, a fluid deodorant, a fluid detergent, a solid detergent, a fluid hard surface cleaner, a solid hard surface cleaner, a fluid fabric refresher spray, a diaper, an air freshening product, a nutraceutical supplement, a controlled release fertilizer, a controlled release insecticide, a controlled release dye and a unit dose detergent further comprising a detergent and a water soluble outer film.

17. A method of making the controlled release particle of claim 2, said method comprising the steps of:

(a) preparing a core material phase by mixing at least one hydrophobic active material with at least one isocyanate resin or prepolymer, at least one epoxy resin or prepolymer, a glycidyloxy alkyl trialkoxy silane, a sugar alcohol and a polymeric plasticizer to make a solution or suspension;

(b) preparing a homogeneous aqueous solution or aqueous dispersion of at least one emulsifier or surfactant and treated protein isolate solution or dispersion;

(c) adding the core material phase into the homogeneous aqueous solution or aqueous dispersion to prepare an oil-in-water emulsion at 20-35° C.;

(d) adjusting a pH and heating the oil-in-water emulsion at 35-40° C. to form a preformed capsule slurry via interfacial polymerization;

(e) adding an aqueous solution of at least one of the at least one AAI adduct, and the at least one AAE adduct into the preformed capsule slurry to form an emulsion;

(f) heating the emulsion to a temperature from 40-60° C. for further polymerization onto a preformed capsule membrane;

(g) adding tetrahydroxy orthosiloxane or orthosilicic acid to the preformed capsule membrane for further cross-linking or polymerization to provide a capsule;

(h) adding a fine powder of amino polysaccharide to form a coacervate on a surface of the capsule;

(i) adding an aqueous dispersion of treated or gelatinized polysaccharide to the capsule to provide a capsule slurry;

(j) optionally, adding preservative into the capsule slurry; and (k) spray drying the capsule slurry to obtain dry powder.

18. The method of claim 17, wherein the at least one emulsifier is a member selected from the group consisting of natural gum, polyvinyl pyrrolidone, copolymer of polyvinyl pyrrolidone with vinyl acetate, vinyl alcohol, vinyl imidazole, polyglycerol oleate, polyvinyl alcohol, ethoxylate nonylphenol, secondary alcohol ethoxylate, water soluble protein, modified polysaccharide, Pickering emulsion stabilizer and chitosan.

* * * * *